(12) United States Patent
Pinczewski et al.

(10) Patent No.: US 6,969,393 B2
(45) Date of Patent: Nov. 29, 2005

(54) APPARATUS FOR USE IN ARTHROPLASTY OF THE KNEES

(75) Inventors: Leo Arieh Pinczewski, Crows Nest (AU); Stephen John Parker, Mosman (AU); Greg Marik, Germantown, TN (US); Richard A. Rocco, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/238,957

(22) Filed: Sep. 10, 2002

(65) Prior Publication Data

US 2003/0153923 A1     Aug. 14, 2003

Related U.S. Application Data

(63) Continuation of application No. PCT/AU01/00262, filed on Mar. 9, 2001.

(51) Int. Cl.[7] .............................................. A61B 17/58
(52) U.S. Cl. ......................................... 606/88; 606/87
(58) Field of Search ............................. 606/88, 80, 86, 606/79, 87; 623/20.21, 20.35, 20.16, 20.19

(56) References Cited

U.S. PATENT DOCUMENTS

| 4,249,878 A | * | 2/1981 | Komarek ..................... 425/237 |
| 4,457,307 A | | 7/1984 | Stillwell |
| 4,719,908 A | * | 1/1988 | Averill et al. ................. 606/80 |
| 4,825,857 A | | 5/1989 | Kenna |
| 5,100,409 A | * | 3/1992 | Coates et al. ................. 606/88 |
| 5,122,144 A | | 6/1992 | Bert et al. |
| 5,171,244 A | | 12/1992 | Caspari et al. |
| 5,514,139 A | | 5/1996 | Goldstein et al. |
| 5,520,695 A | | 5/1996 | Luckman |
| 5,597,379 A | | 1/1997 | Haines et al. |
| 5,643,272 A | * | 7/1997 | Haines et al. ................. 606/80 |
| 5,735,904 A | | 4/1998 | Pappas |
| 5,755,803 A | | 5/1998 | Haines et al. |
| 5,810,827 A | * | 9/1998 | Haines et al. ................. 606/80 |
| 5,824,098 A | * | 10/1998 | Stein ....................... 623/20.18 |
| 5,830,216 A | | 11/1998 | Insall et al. |
| 5,879,354 A | * | 3/1999 | Haines et al. ................. 606/86 |
| 5,897,559 A | * | 4/1999 | Masini ........................ 606/86 |

(Continued)

FOREIGN PATENT DOCUMENTS

EP         857463 A2      8/1998

(Continued)

Primary Examiner—Pedro Philogene
(74) Attorney, Agent, or Firm—Kilpatrick Stockton LLP

(57) ABSTRACT

A cutting device for being inserted into a knee joint between the tibia and the femur, wherein the cutting device is adapted for resecting bone from the femur to a desired depth in a path of travel of the tibia when located in the knee joint and operated as the tibia is moved through an arc of motion about the femur between backward and forward positions. A cutting device is also disclosed for being inserted into a knee joint between the tibia and the femur for resecting bone from the tibia to a desired depth to form a recess in a condyle of the tibia for reception of a tibial implant, comprising a body being located between the tibia and the femur, a cutter for resecting the bone from the tibia to form the recess and a drive mechanism for driving the cutter to resect the bone and being arranged in the body, wherein the cutter is mounted on the body and protrudes therefrom for resecting the bone from the tibia.

52 Claims, 25 Drawing Sheets

U.S. PATENT DOCUMENTS

| | | |
|---|---|---|
| 6,013,081 A | 1/2000 | Burkinshaw et al. |
| 6,056,754 A | 5/2000 | Haines et al. |
| 6,132,468 A * | 10/2000 | Mansmann ............... 623/20.16 |
| 6,197,064 B1 | 3/2001 | Haines et al. |
| 6,488,687 B1 * | 12/2002 | Masini ........................ 606/88 |
| 2002/0029038 A1 | 3/2002 | Haines |

FOREIGN PATENT DOCUMENTS

| | | |
|---|---|---|
| EP | 0 914 806 A1 | 5/1999 |
| WO | WO 91/10408 | 7/1991 |
| WO | WO 96/07361 | 3/1996 |
| WO | WO 01/66021 A1 | 9/2001 |
| WO | WO 01/66022 A1 | 9/2001 |

* cited by examiner

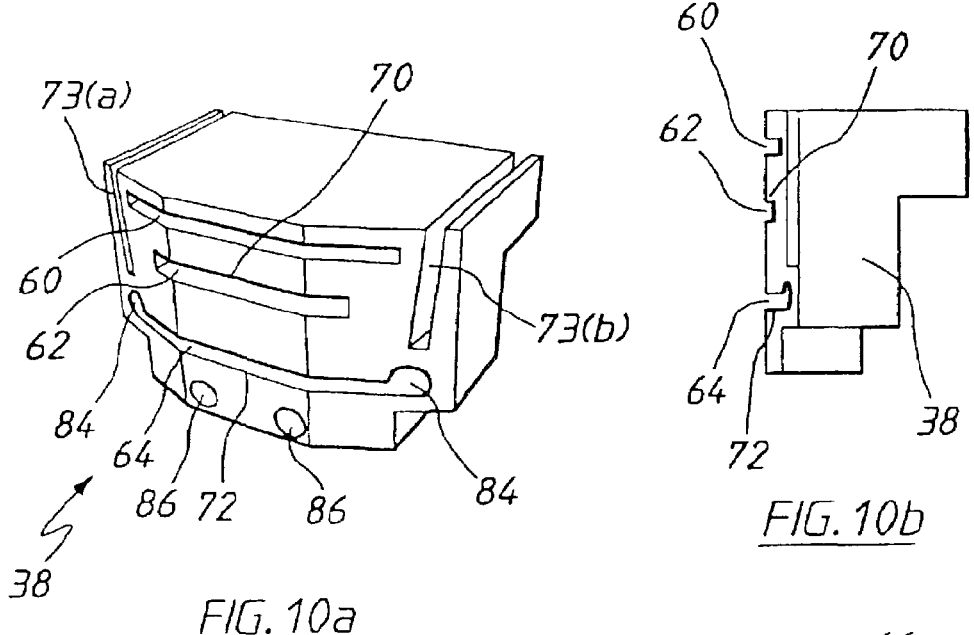
FIG. 10a
FIG. 10b
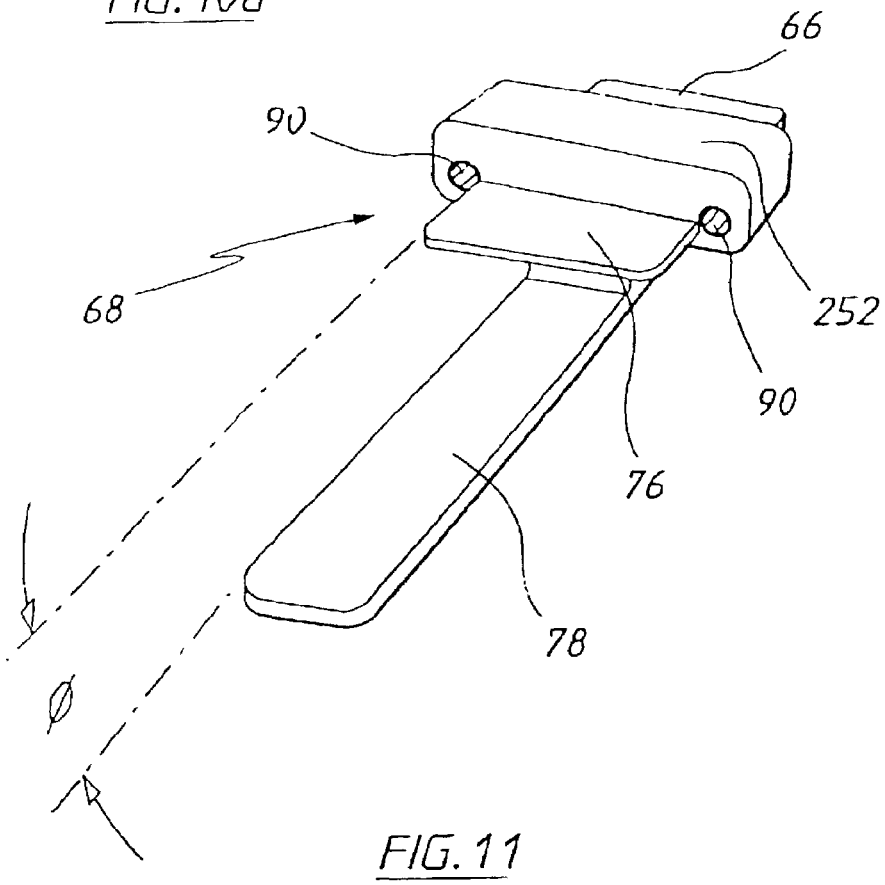
FIG. 11

APPARATUS FOR USE IN ARTHROPLASTY OF THE KNEES

CROSS-REFERENCE TO RELATED APPLICATIONS

This application is a continuation of International Application No. PCT/AU01/00262 filed on Mar. 9, 2001 and published in English as International Publication Number WO 01/66022 A1 on Sep. 13, 2001, which claims priority to Australian Patent Application No. PQ 6161 filed on Mar. 10, 2000, Australian Patent Application No. PQ 8999 filed on Jul. 25, 2000, Australian Patent Application No. PQ 9044 filed on Jul. 27, 2000, and Australian Patent Application No. PQ 9045 filed on Jul. 27, 2000.

FIELD OF THE INVENTION

The present invention relates to apparatus for use in arthroplasty on a knee joint and methods utilising the apparatus.

BACKGROUND OF THE INVENTION

Various methods and apparatus for performing knee arthroplasty and unicondylar knee arthroplasty in particular, are known in the art. The known methods involve resection of the tibia and femur for fitting of trial tibial and femoral implants, respectively. Once the bone has been resected and the trial implants are secured in place, the surgeon then assesses the kinematics of the knee joint. At this stage, the surgeon may transect, elevate and/or release ligaments and other soft tissue structures to achieve the desired level of deformity correction, balance in the tension of relevant ones of the ligaments and other stabilising soft tissue structures, and an acceptable range of motion of the knee joint. Additional bone resection may also be required to achieve the desired outcome. This leads to an increase in operation time with an associated increase in the risk of surgery related complications. Such additional surgical intervention following fitting of the trial implants potentially leads to subsequent increased discomfort for the patient and increased healing times.

Accordingly, it is desirable that surgical intervention be minimised and operating times decreased.

Methods and apparatus for use in arthroplasty of a knee joint are exemplified in U.S. Pat. No. 5,171,244 and U.S. Pat. No. 5,520,695.

SUMMARY OF THE INVENTION

It is an aim of the present invention in at least one form thereof to provide apparatus for use in arthroplasty on a knee joint.

A method of arthroplasty as described herein may involve preparing a femur for the fitting of a femoral prosthesis to the femur, comprising:
(a) locating a cutting device in a knee joint between the femur and the tibia;
(b) moving the tibia through an arc of motion about the femur between backward and forward positions while the cutting device is being operated and located between the femur and the tibia to thereby resect bone from the femur to a desired depth in a direction of travel of the tibia relative to the femur.

The method may also comprise securing a tibial implant on the tibia prior to locating the cutting device in the knee joint between the femur and the tibia. Preferably, the locating will comprise locating the cutting device on the tibial implant, and the cutting device will be retained on the tibial implant during the rotation of the tibia about the femur.

Preferably, the method will further comprise resecting bone from the tibia to provide a prepared surface on which the tibial implant is subsequently positioned. The resection of the bone from the tibia may comprise resecting bone from the tibia to a desired depth to form a recess in the tibia for positioning of the tibial implant on the tibia.

Rather than positioning the cutting device on a tibial implant, it may be seated directly on the tibia and more preferably, within a recess resected into the end of the tibia adjacent to the femur.

Accordingly, a method of arthroplasty may involve preparing a tibia for the fitting of a tibial implant on the tibia, comprising:
(a) locating a cutting device in a knee joint between the femur and the tibia; and
(b) resecting bone from the tibia utilising the cutting device to form a recess having a desired profile in a condyle of the tibia for receiving the tibial implant.

In addition, the method may further comprise:
securing a guide jig in position about the knee joint for guiding movement of the cutting device relative to the tibia;
positioning the cutting device on the guide jig; and
moving the cutting device relative to the tibia whereby the movement of the cutting device is guided by the guide jig to thereby form the recess to the desired profile.

There is also provided apparatus for use in the above methods. Embodiments of apparatus described herein may be provided assembled or in kit form.

Hence, in an aspect of the present invention there is provided a cutting device for being inserted into a knee joint between the tibia and the femur, wherein the cutting device is adapted for resecting bone from the femur to a desired depth in a path of travel of the tibia when located in the knee joint and operated as the tibia is moved through an arc of motion about the femur between backward and forward positions.

Preferably, the cutting device will be adapted for being seated on a tibial implant secured in position on the tibia.

Preferably, the cutting device has an upperside and an opposite underside, and has a guide member depending from the underside for insertion into a channel of the tibial implant for thereby guiding insertion of the cutting device into the knee joint. The guide member may be for instance be a depending boss or longitudinally extending key.

Most preferably, the cutting device will be adapted for inhibiting lifting of the cutting device from the tibial implant during movement of the tibia about the femur.

Typically, the cutting device will incorporate a body for being inserted into the knee joint and which is provided with cutting means for facilitating the cutting of the bone from the femur. The cutting means may comprise a rotatable cutter for resecting the bone from the femur.

In another aspect of the present invention there is provided a cutting device in combination with a tibial implant on a tibia, wherein the cutting device rests on the tibial implant and is adapted for resecting bone from the femur to a desired depth in a path of travel of the tibia while being operated and with movement of the tibia through an arc of motion about the femur between backward and forward positions.

In yet another aspect of the present invention there is provided a cutting device for resecting bone to a desired depth from a femur, comprising:
(a) a body for being inserted into a knee joint between the femur and the tibia;
(b) a rotatable cutter for being rotated relative to the body to resect the bone from he femur; and
(c) a drive mechanism for driving the rotation of the cutter and being carried by the body;
   wherein the cutter is mounted on the body and stands proud for resection of the femur in a path of travel of the tibia through an arc of motion about the femur between backward and forward positions.

Preferably, the body has an upperside from which the cutter protrudes, and an opposite underside for resting on a tibial implant on the tibia.

Preferably, the cutter will be readily removable from the cutting device. Generally, the cutter will have a concaved upper surface.

Preferably, the cutter will have a plurality of radially projecting blades for resecting the bone from the femur to the desired depth.

Preferably, each respective blade will have a cutting edge defined on a leading side of the blade and a further cutting edge on an outer peripheral end of the blade. In addition, each blade will usually have a thickness which decreases from the leading side of the blade to a trailing side of the blade.

Most preferably, the cutter will be adapted for cutting a channel into the femur along the path of travel to a depth greater than the desired depth, simultaneously with the resection of the bone to said desired depth.

Preferably, the cutter will incorporate a toothed gear for being rotatably driven by a drive mechanism arranged within the cutting device for driving rotation of the cutter.

Preferably, the cutting device will comprise a head carrying the cutter, and a body for being attached to a power tool for driving rotation of the cutter, wherein the head is detachably coupled with the body.

In yet another aspect of the present invention there is provided a cutting device for being inserted into a knee joint between the tibia and the femur for resecting bone from the tibia to a desired depth to form a recess in a condyle of the tibia for reception of a tibial implant, and comprising;
a) a body for being located between the tibia and the femur;
b) a cutter for resecting the bone from the tibia to form the recess; and
c) a drive mechanism for driving the cutter to resect the bone and being arranged in the body;
wherein the cutter is mounted on the body and protrudes therefrom for resecting the bone from the tibia.

Preferably, the body will be adapted for being supported by a support mounted in position about the knee joint, when the cutting device is located in the knee joint between the tibia and the femur.

In a further aspect of the present invention there is provided a cutting device for resecting bone from the tibia to form a recess for receiving a tibial implant, wherein the cutting device is adapted for being inserted into a knee joint between the tibia and the femur for resecting the bone from the tibia to form the recess, and for being mounted on a guide jig secured in position about the tibia for guiding the resection of the bone by the cutting device.

Preferably, the cutting device will comprise a body carrying a rotatable cutter wherein he body is recessed or otherwise adapted for overlying a peripheral region of the tibia when he cutting device is mounted on the guide jig.

In a yet further aspect of the present invention there is provided an assembly for resecting bone from the tibia to form a recess for receiving a tibial implant, wherein the assembly comprises a cutting device adapted for being inserted into a knee joint between the tibia and the femur for resecting the bone from the tibia, and a guide jig adapted for guiding movement of the cutting device relative to the tibia to enable shaping of the recess to a desired profile by the cutting device.

Preferably, the guide jig incorporates a template for guiding the movement of the body of the cutting device relative to the tibia. The template of the jig may be a recess defined in the jig. Typically, the cutting device will be provided with a guide pin that projects into the recess of the jig for facilitating the guiding of the cutting device. In another embodiment, the guide jig may comprise a pentagraph arrangement on which the cutting device is arranged.

In still another aspect of the present invention there is provided a guide jig for reception of a cutting device for resecting bone from an end of a tibia to form a recess in the tibia for receiving a tibial implant, wherein the guide jig is adapted for being secured in position about a knee joint and incorporates a template for guiding movement of the cutting device relative to the tibia for shaping of the recess to a desired profile.

Preferably, the guide jig will be adapted for being secured to the tibia.

In another aspect of the present invention there is provided a tibial implant for being secured in position in a knee joint on a resected surface of a condyle of the tibia for evaluating movement of the tibia about the femur through an arc of motion between backward and forward positions prior to removal of the tibial implant for allowing a corresponding tibial prosthesis to be mounted on the tibia in said position, wherein the tibial implant is adapted for locating a cutter device in a desired orientation relative to the femur for guiding resection of the femur to a desired depth with travel of the tibia about the femur between the backward and forward positions.

In a yet still further aspect of the present invention there is provided a tibial implant for being inserted into a knee joint and mounted on an end of the tibia adjacent to the femur, wherein the tibial implant comprises a body with an upperside face and an opposite underside face for being seated in position on the tibia, and wherein a channel for receiving a cutting device for resection of bone from the femur and orientated in a substantially forward to rearward direction is defined in the upperside face of the body.

Preferably, the tibial implant will be adapted for orientating the cutter device in an anterior to posterior direction of the knee joint.

Preferably, the tibial implant will be adapted for being mated with the cutter device for inhibiting lifting of the cutter device from the tibial implant during the movement of the tibia about the femur.

Preferably, a channel is defined in the tibial implant for reception of the cutter device for thereby orientating the cutter device in the anterior to posterior direction of the knee joint.

Most preferably, the tibial implant is a tibial trial.

In another aspect of the present invention there is provided a cutter for resecting bone to a desired depth from the femur of a knee joint and which is adapted for being rotatably mounted on a cutting device for being inserted into the knee joint between the femur and the tibia for the resection of the bone from the femur by the cutter in a path of travel of the tibia as the tibia is moved through an arc of motion about the femur between backward and forward positions.

In a further aspect of the present invention there is provided a cutter for resecting bone from the femur of a knee joint and which is adapted for being rotatably mounted on a cutter device for insertion into the knee joint between the femur and the tibia, comprising;

a) one or more blades for resecting bone from the femur to a desired depth along a path of travel of the tibia with movement of the tibia through an arc of motion about the femur between backward and forward positions; and b) a further blade for simultaneously cutting a channel into the femur to a greater depth along the path of travel.

Preferably, the cutter will be in the form of a disk and the further blade for resecting the channel into the femur will be centrally located on the disk.

The further blade of the cutter will usually be dimensioned such that the resulting channel resected into the femur will be capable of accommodating a fin of a femoral prosthesis. By resecting the channel into the femur at the same time as resecting the layer of bone therefrom, operating time may be reduced and the channel may be formed with greater accuracy.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The features and advantages of the present invention will become further apparent from the following detailed description of a number of preferred embodiments illustrated in the accompanying drawings.

BRIEF DESCRIPTION OF THE ACCOMPANYING DRAWINGS

FIG. 10(a) is a rear perspective view of a guide jig of the apparatus shown in FIG. 8;

FIG. 10(b) is a side view of the guide jig of FIG. 10(a);

FIG. 11 is a view of an alignment component of the apparatus shown in FIG. 8.

Figure 8:
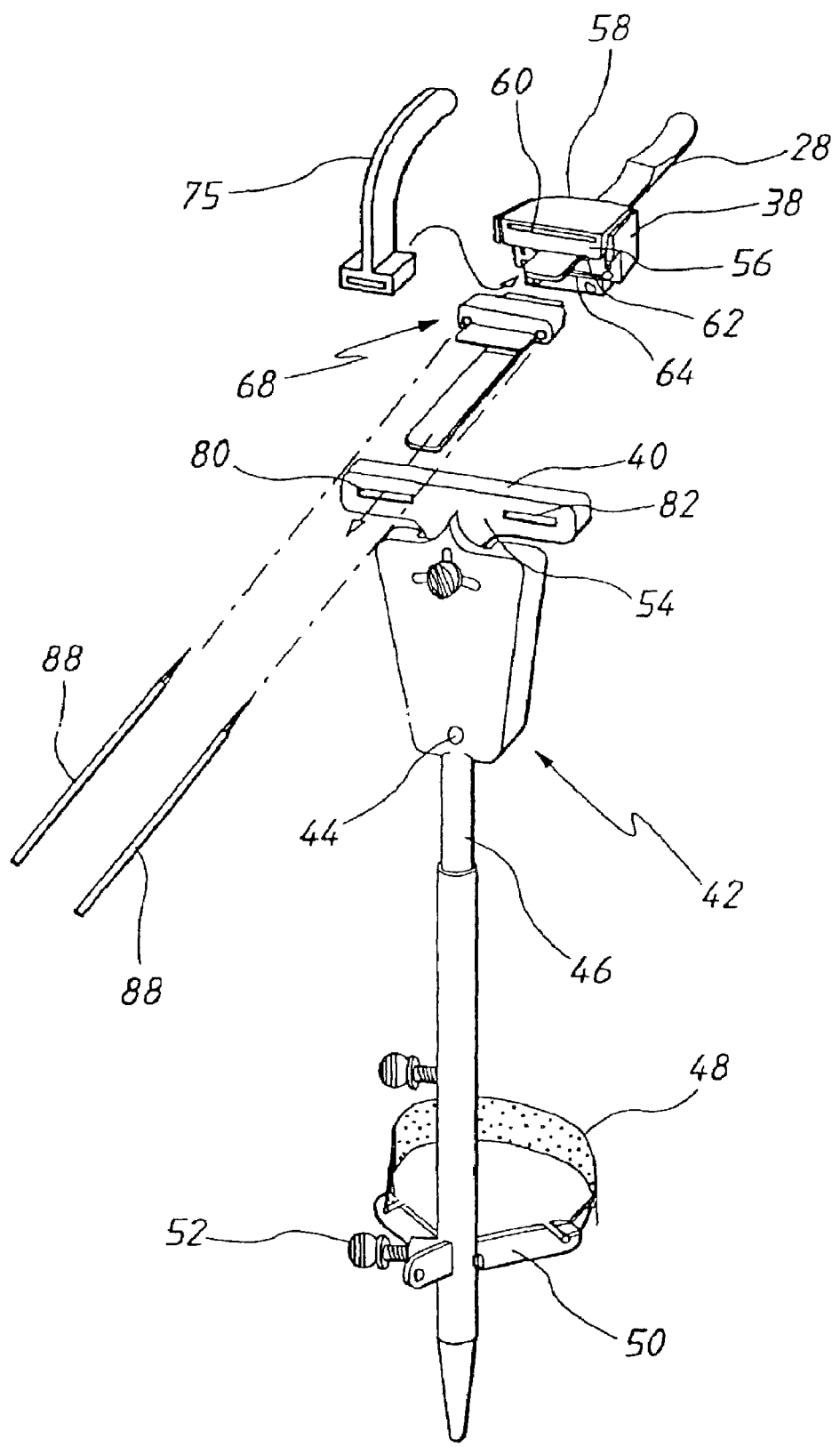
FIG. 8 is a perspective exploded view of apparatus for performing arthroplasty on a knee joint.
Figure 33A:
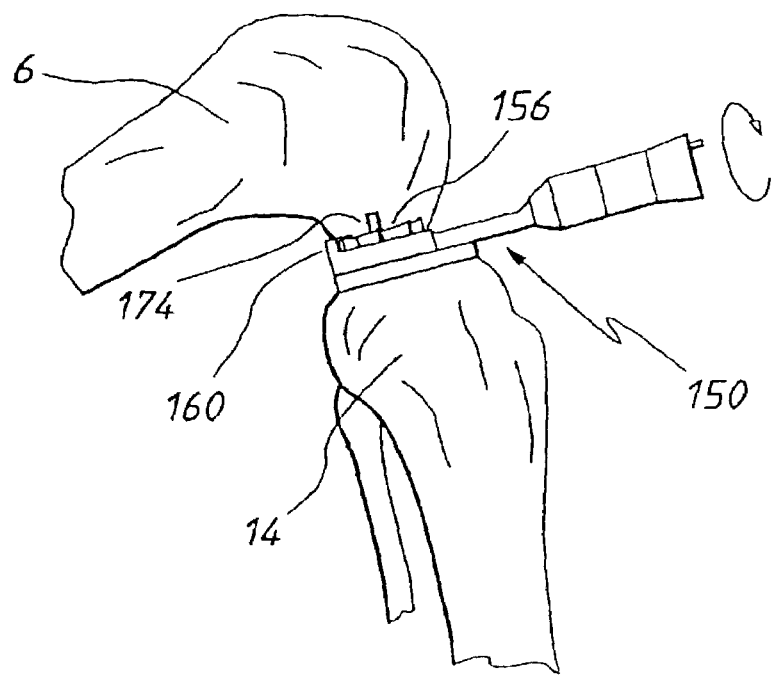
Figure 33B:
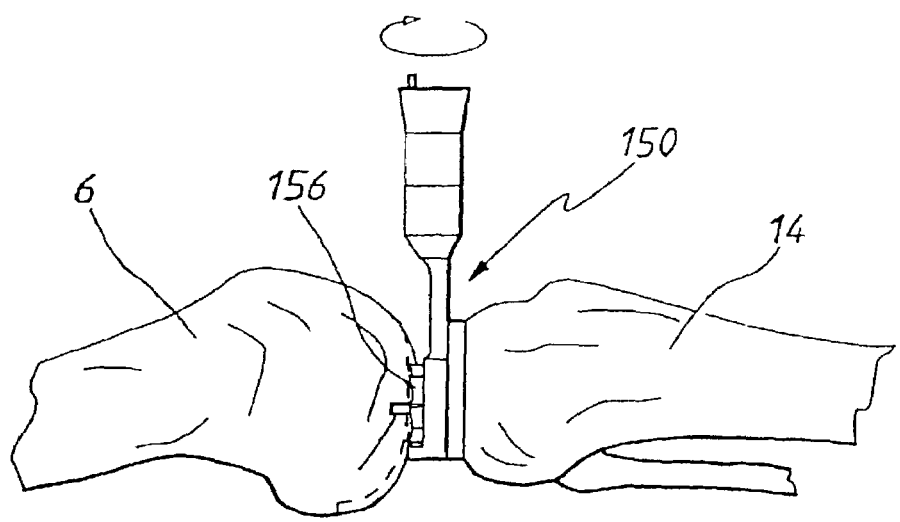
Figure 33C:
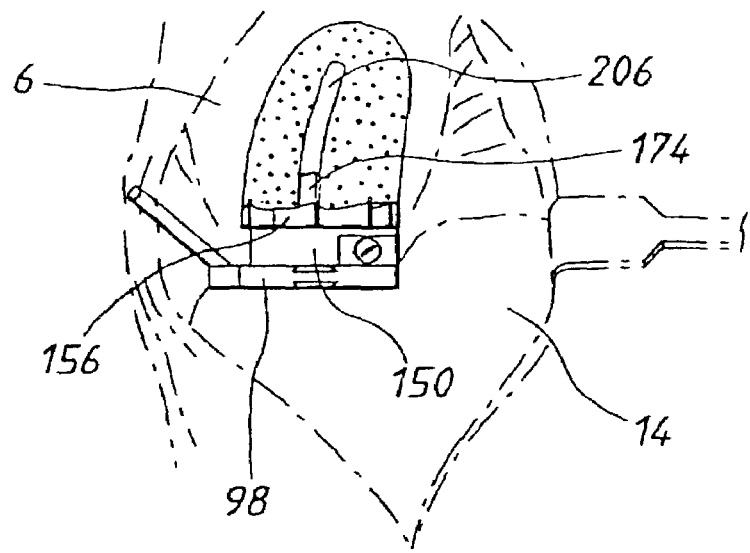
Figure 34:
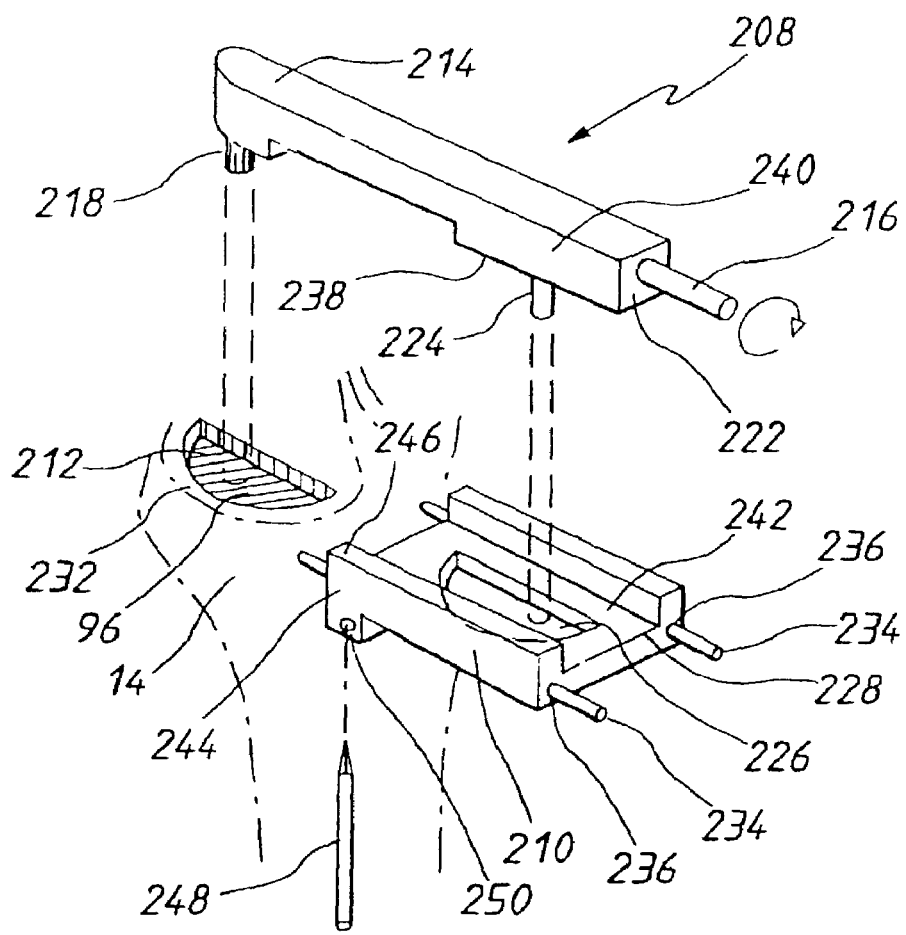
Figure 35:
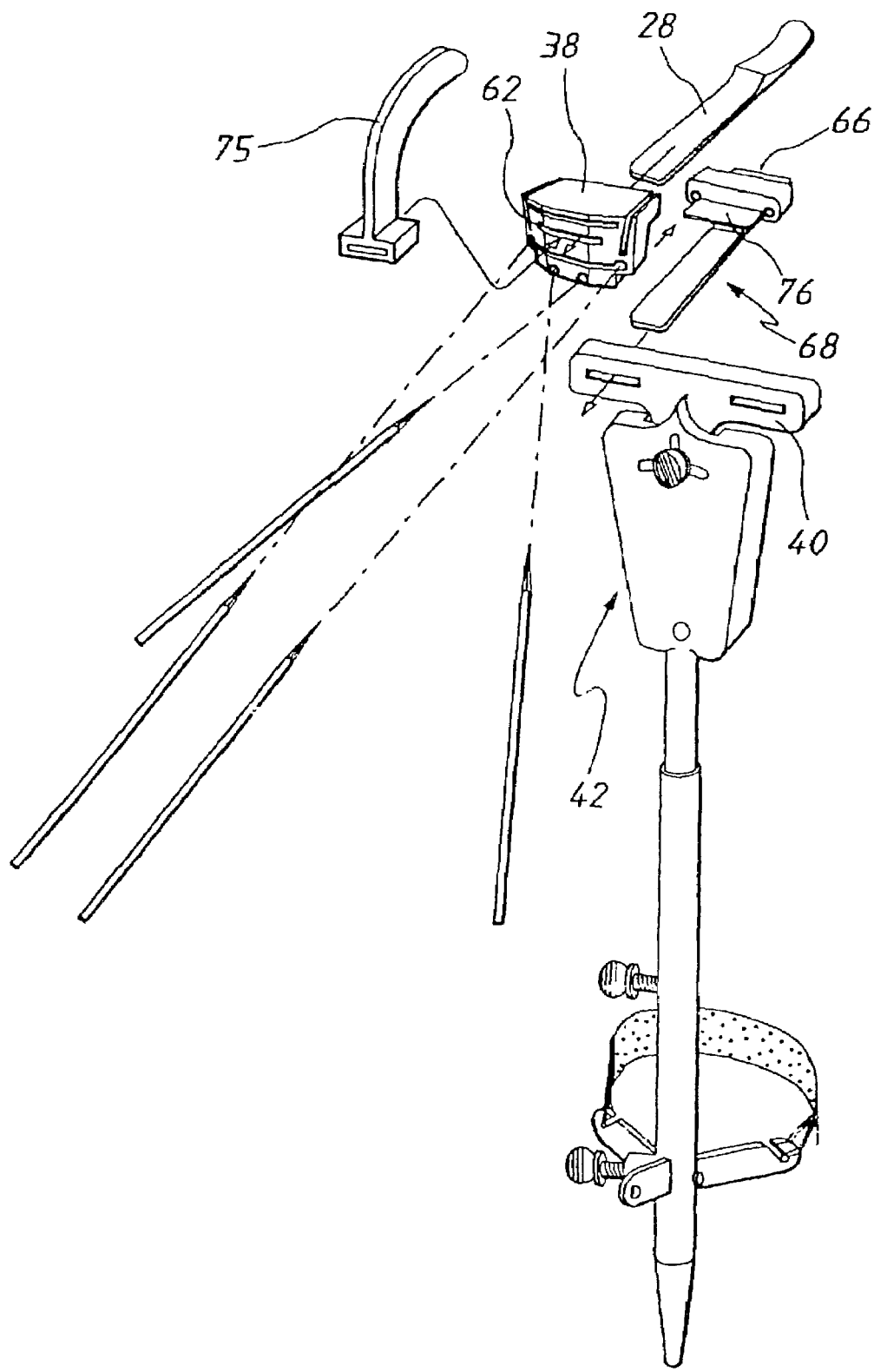
Figure 36:
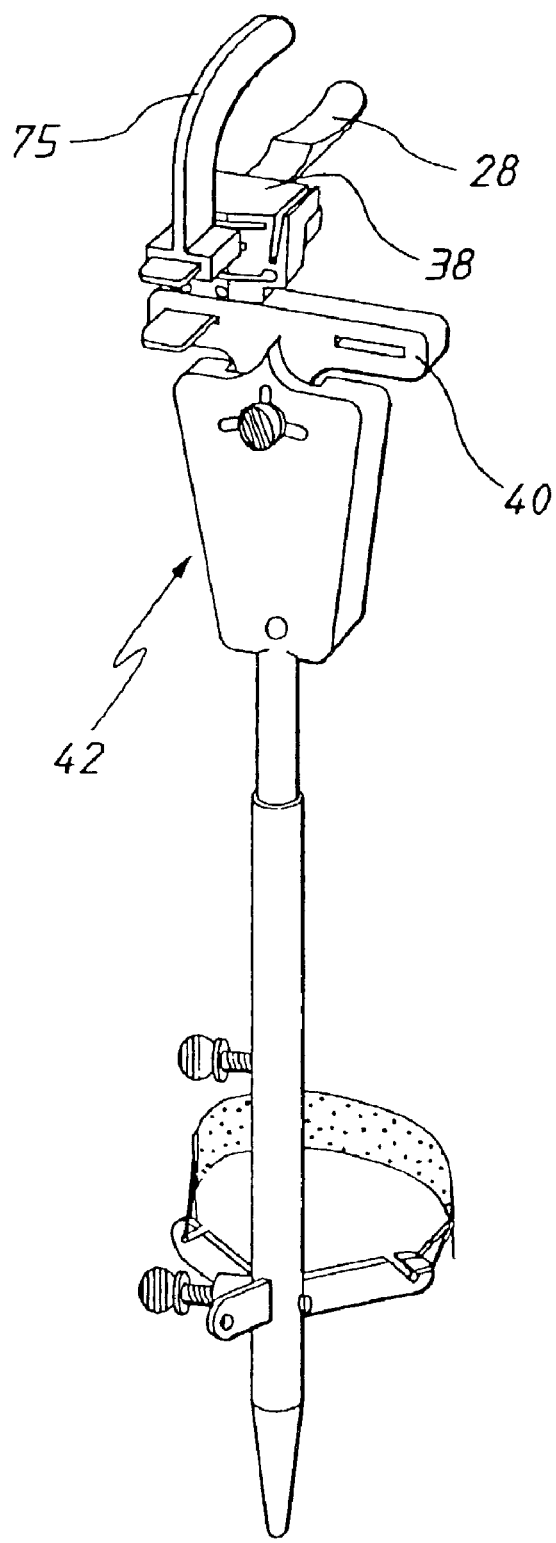
Figure 37:
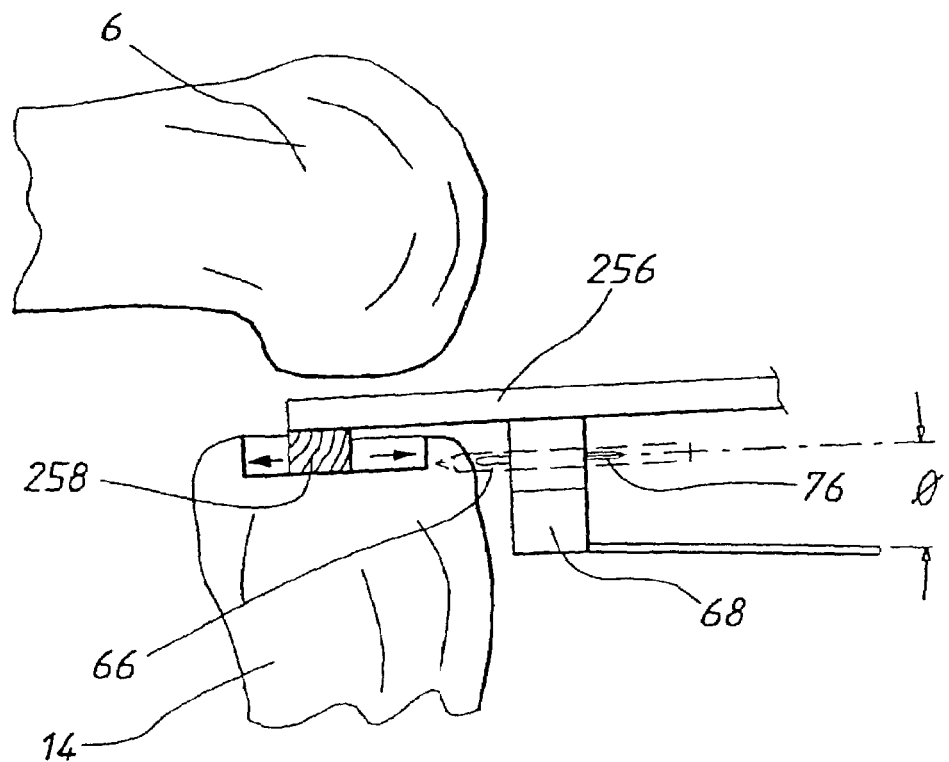
Figure 38:
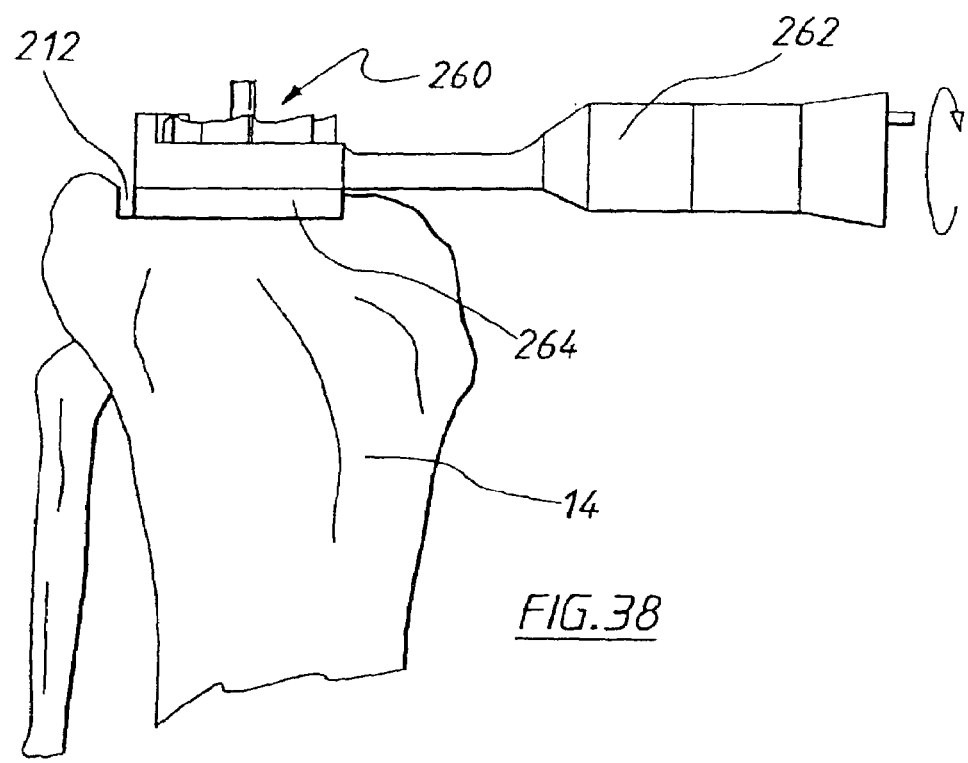

FIGS. 33(a) to 33(c) illustrate the resection of bone to a desired depth from the femur;

FIG. 34 is an exploded perspective view of an assembly for forming a recess in the tibia for receiving a tibial implant;

FIG. 35 is an exploded perspective view of the apparatus of FIG. 8 when arranged for removal of bone from the tibia for inset placement of a tibial implant;

FIG. 36 is a perspective view of the apparatus arranged as shown in FIG. 35 when assembled;

FIG. 37 illustrates removal of bone from the tibia for inset tibial implant placement utilising apparatus of the invention; and FIG. 38 illustrates a further cutting device for resecting bone to a desired depth from the femur.

DETAILED DESCRIPTION OF PREFERRED EMBODIMENTS OF THE PRESENT INVENTION

Figure 1:
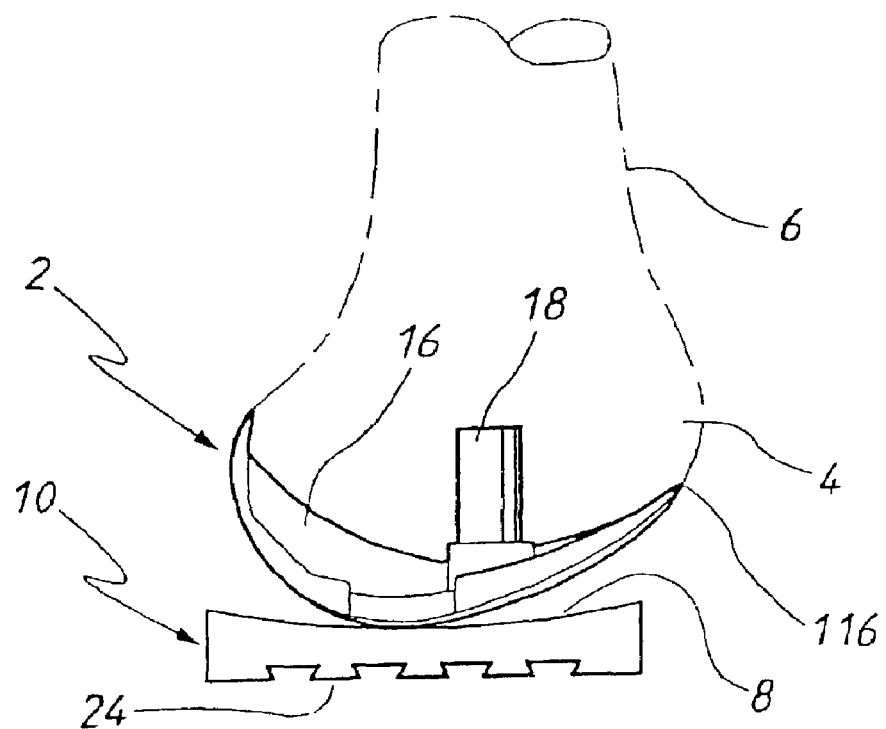
FIG. 1 is a side schematic view illustrating a knee joint with tibial and femoral prostheses fitted.
Figure 2:
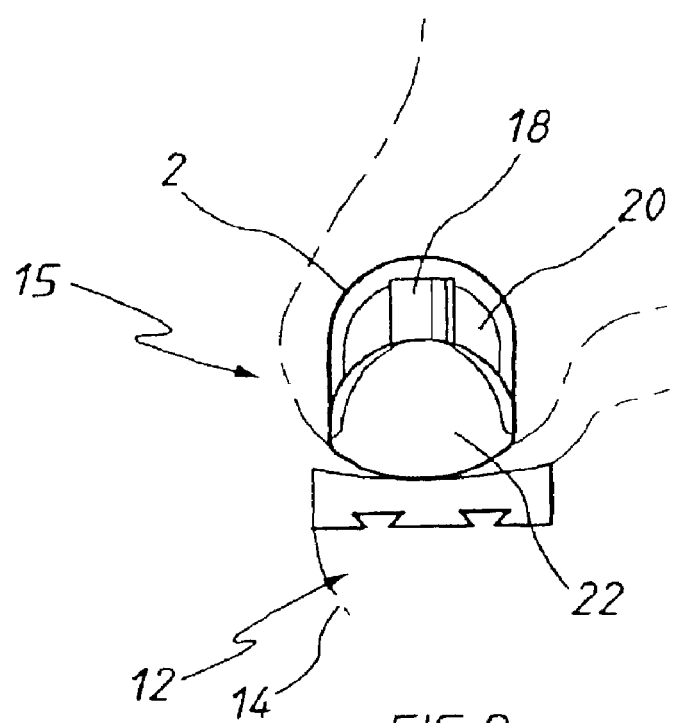
FIG. 2 is an anterior view of the fitted tibial and femoral prostheses shown in FIG. 1.

The femoral prosthesis 2 shown in FIG. 1 is fitted to the medial condyle 4 of the femur 6 and abuts articulating surface 8 of the tibial prosthesis 10 fitted on the corresponding medial condyle 12 of the tibia 14, for articulation thereon as the tibia undergoes flexion and extension about the knee joint 15. The positioning of the femoral prosthesis 2 and the tibial prosthesis 10 is more clearly shown in FIG. 2.

Figure 3:
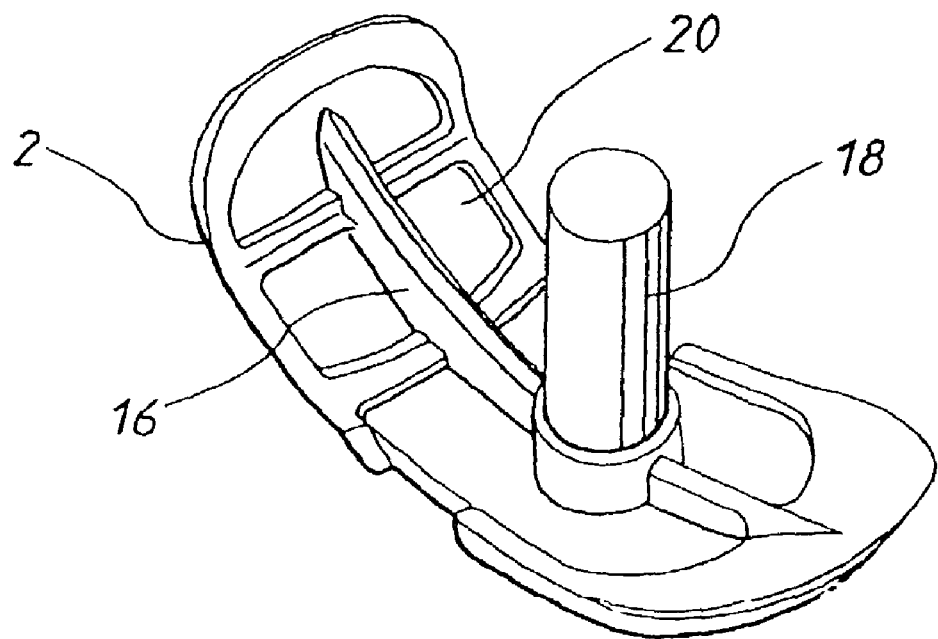
FIG. 3 is a perspective view of the femoral prostheses shown in FIG. 1 prior to being fitted.

As shown in FIG. 3, the femoral prosthesis 2 is provided with a centrally orientated upstanding fin 16 incorporating a peg 18 projecting from an interior face 20 of the prosthesis. The opposite outer face 22 has a curved contour for facilitating movement of the tibia about the femur. The interior face 20 of the femoral prosthesis is textured to enhance binding of bonding cement used to fix the prosthesis to the femur. The prosthesis itself is formed from a cast cobalt chromium molybdenum alloy conventionally used in the manufacture of such prostheses.

Figure 4:
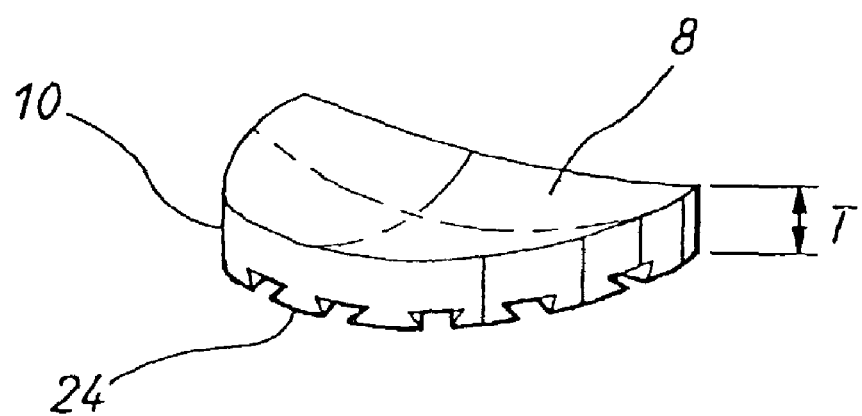
FIG. 4 is a perspective view of the tibial prostheses shown in FIG. 1 prior to being fitted.

The tibial prosthesis 10 shown more clearly in FIG. 4 is manufactured from ultra high molecular weight polyethylene and has a dove tailed base 24 to again enhance bonding of cement to the prosthesis for fixing the prosthesis to the tibia. The articulating surface 8 of the tibial prosthesis is sightly concaved to substantially match curvature of the outer face 22 of the femoral prosthesis.

Figure 5:
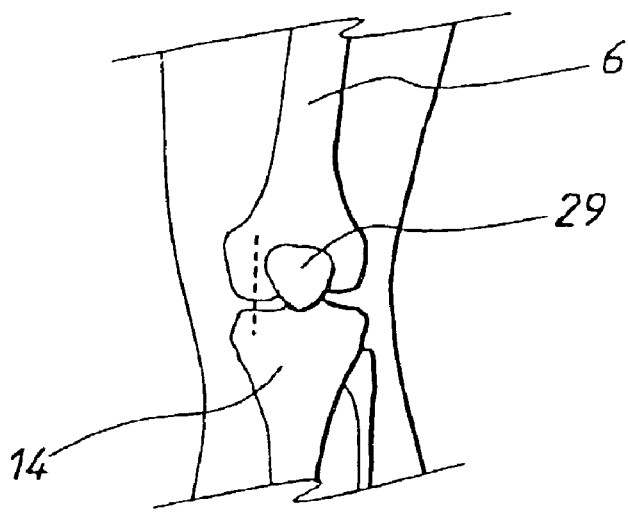
FIG. 5 is a diagrammatic front view of a knee joint.

An example of unicondylar arthroplasty will now be described. As a first step, a longitudinal incision is made in the knee from just medial to the medial edge of the patella 26 to just below the medial tibial plateau adjacent to the attachment of the iliotibial tract, as indicated by the dotted line in FIG. 5. The incision avoids transecting any of the ligamentous structures that contribute to the kinematics of the knee. The patella is not everted, but gently retracted laterally to expose the medial compartment of the knee. All femoral and tibial osteophytes which are accessible are then removed.

Figure 6:
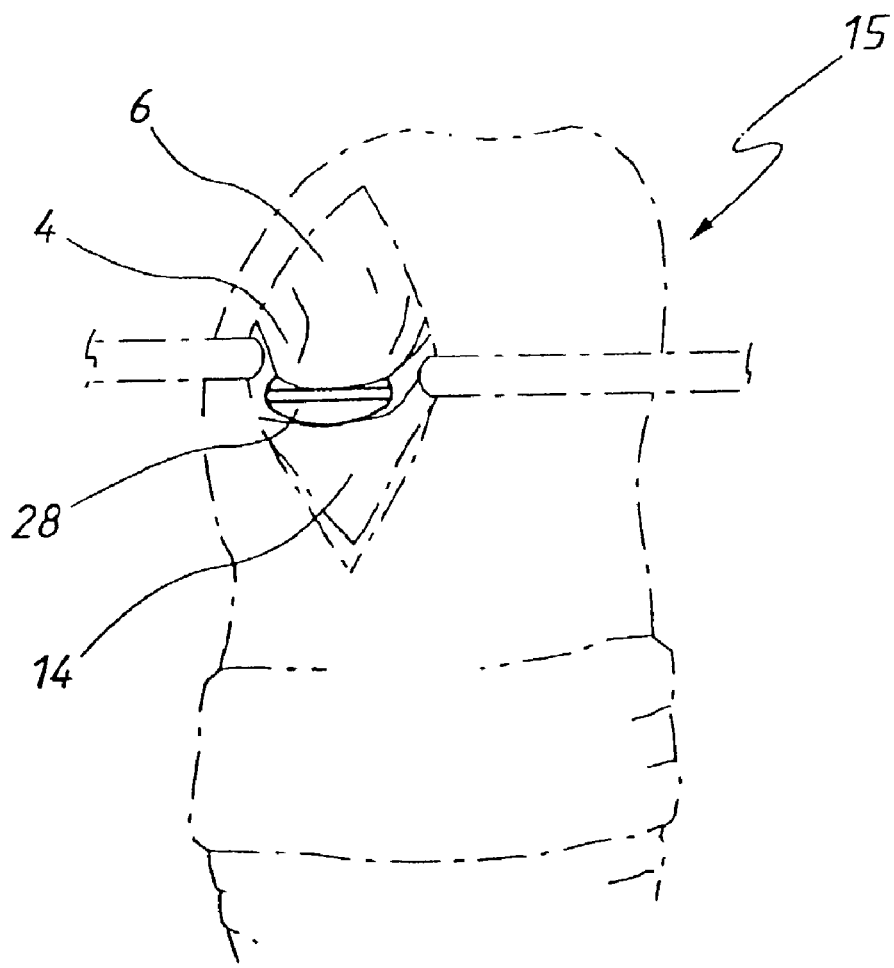
FIG. 6 is a diagrammatic front view showing a spacer in position between a femur and a tibia of the knee joint illustrated in FIG. 5.

In order to balance tension in ligaments and other soft tissue structures of the knee joint as well as to correct deformity, a spacer 28 is located in position between the condyle of the femur and the corresponding condyle of the tibia as shown in FIG. 6. The spacer effectively spaces the femur from the tibia.

To check for adequate tension of the soft tissue structures and kinematics of the knee joint, the tibia is moved through an arc of flexion of between 0° to about 130°. If the knee joint is unstable or has inadequate tension, the spacer may be removed and a spacer having a greater thickness for spacing the tibia and the femur further apart may be located in the joint. Conversely, if the knee feels over tensioned or adequate range of movement through the arc of flexion cannot be achieved, the spacer may be replaced with a spacer having a reduced thickness to decrease the spacing between the femur and the tibia. This process may be repeated a number of times using a spacer having a different thickness each time until adequate tension and kinematics of the knee joint is achieved.

Importantly, the method enables the tensioning of soft tissue structures in the knee joint to be optimised prior to any bone being resected from the tibia or the femur in preparation for fitting of the tibial and femoral prostheses. Moreover, the tensioning may be obtained without the need to transect, elevate or release soft tissue structures of the knee joint. However, further adjustment of the tensioning in the knee joint as may be deemed necessary using such procedures is not excluded.

Figure 7:
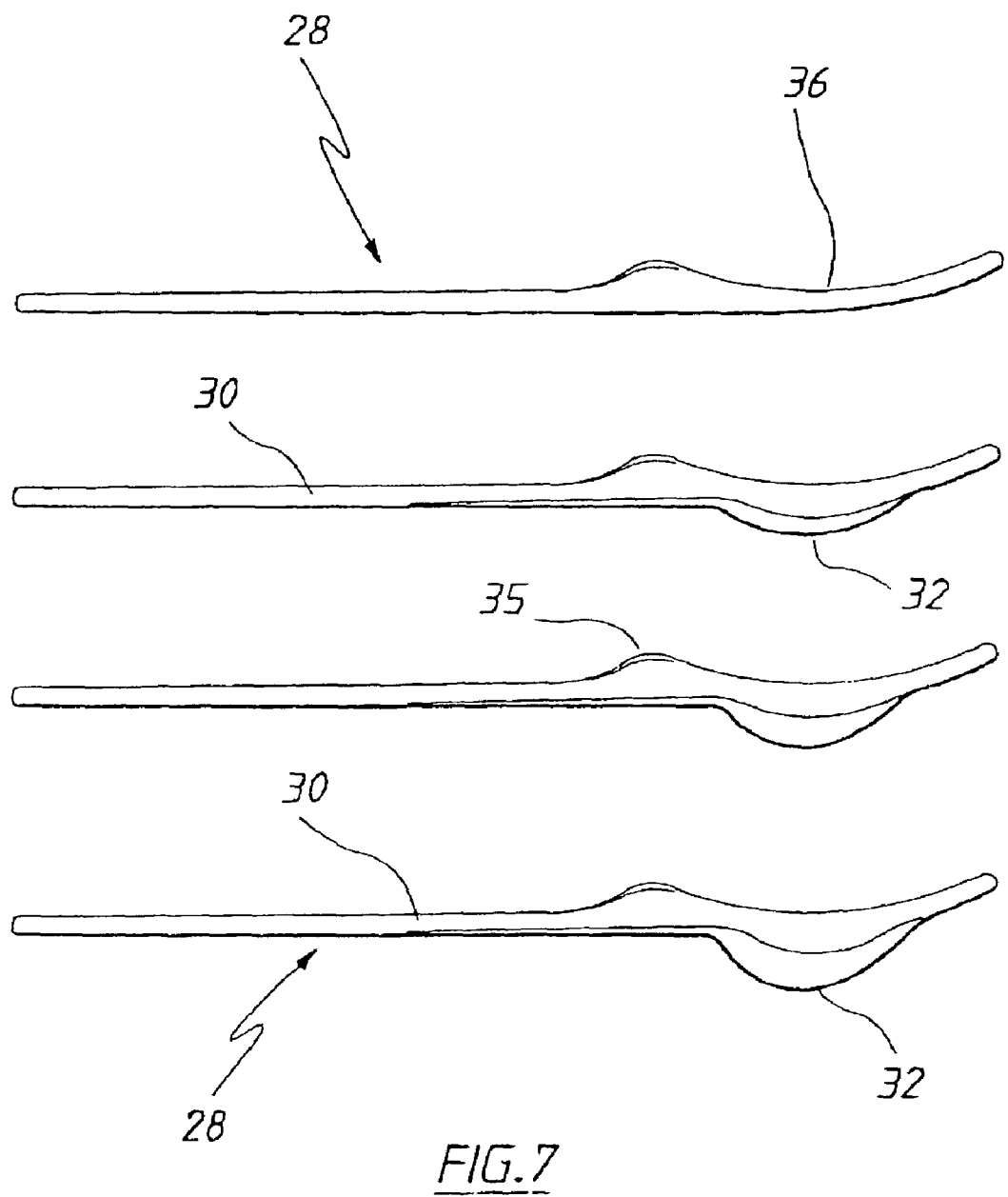
FIG. 7 is a diagrammatic side view of a set of different spacers, for providing different spacing of the femur from the tibia.

A set of spacers from which the appropriate spacer 28 may be selected is illustrated in FIG. 7. The spacers each comprise an elongate body 30 for being inserted into the knee joint between opposing condyles of the tibia and the femur. The body 30 has a bulbous protrusion 32 formed on an underside of a leading end region 34 thereof for being seated on the sulcus of the relevant tibial condyle. As can be seen, the leading end region of each spacer is scooped upwardly forward of transverse ridge 35 thereby defining a trough 36 for receiving the condyle of the femur. The scooped contour of the leading end region of the spacer facilitates insertion of the spacer into the knee joint and assists in retaining the spacer in position once located in the knee joint.

As will be appreciated, the spacing of the femur from the tibia is determined by the thickness of the bulbous protrusion. In the spacer set shown, the thickness of the respective spacers increases in 1 mm increments. However, sets of spacers having a different thickness range may of course be used instead.

Once the appropriate spacer 28 has been selected and located in position in the knee joint, apparatus as shown in FIG. 8 for guiding cutting of the tibia and the femur for resection of bone therefrom is secured in position about the knee joint. The apparatus comprises a guide jig in the form of a tibiofemoral cutting block 38 adapted for being securely mounted on mounting platform 40 of tibial alignment guide 42.

Tibial alignment guide 42 is adapted for being aligned along the longitudinal axis of the tibia and the mounting platform 40 is able to be angularly adjusted relative thereto about pivot 44 to accommodate required varus or valgus adjustment in the medial to lateral direction of the knee joint as may be necessary. Angular displacement of the mounting platform is achieved by loosening lock nut 52 and rotating the platform about the pivot pin 44 to the desired angle with reference to a scale (not shown) marked on the front face 54 of the tibial alignment guide, and subsequently retightening the lock nut 52. Shaft 46 of the alignment guide is telescopic to permit an ankle strap 48 carried on the bracket 50 mounted on the lower end region of the alignment guide to be secured around the ankle.

A more detailed view of the cutting block 38 is shown in FIG. 10(a). As indicated, a number of slots extending through the cutting block from a front face 56 to an opposite rear face indicated by the numeral 58 are defined in the cutting block. In particular, the cutting block incorporates an upper slot 60 for guiding cutting of the femur in the resection of bone therefrom, and a middle slot 62 for receiving the protruding end region of the spacer when inserted in the knee joint. A lower slot 64 is also defined in the cutting block for reception of rear tongue 66 of alignment component 68. The distance between the top 70 of the slot 62 and the bottom 72 of the lower slot 64 corresponds essentially to the thickness T of the tibial prosthesis 10 of FIG. 4. A pair of inwardly directed channels 73(a) and 73(b) are also defined in opposite side regions of the cutting block, one in each side region respectively, for guiding downwardly directed cuts into the tibia in the resection of bone therefrom. A side view of the cutting block 38 is shown in FIG. 10(b).

Figure 9A:
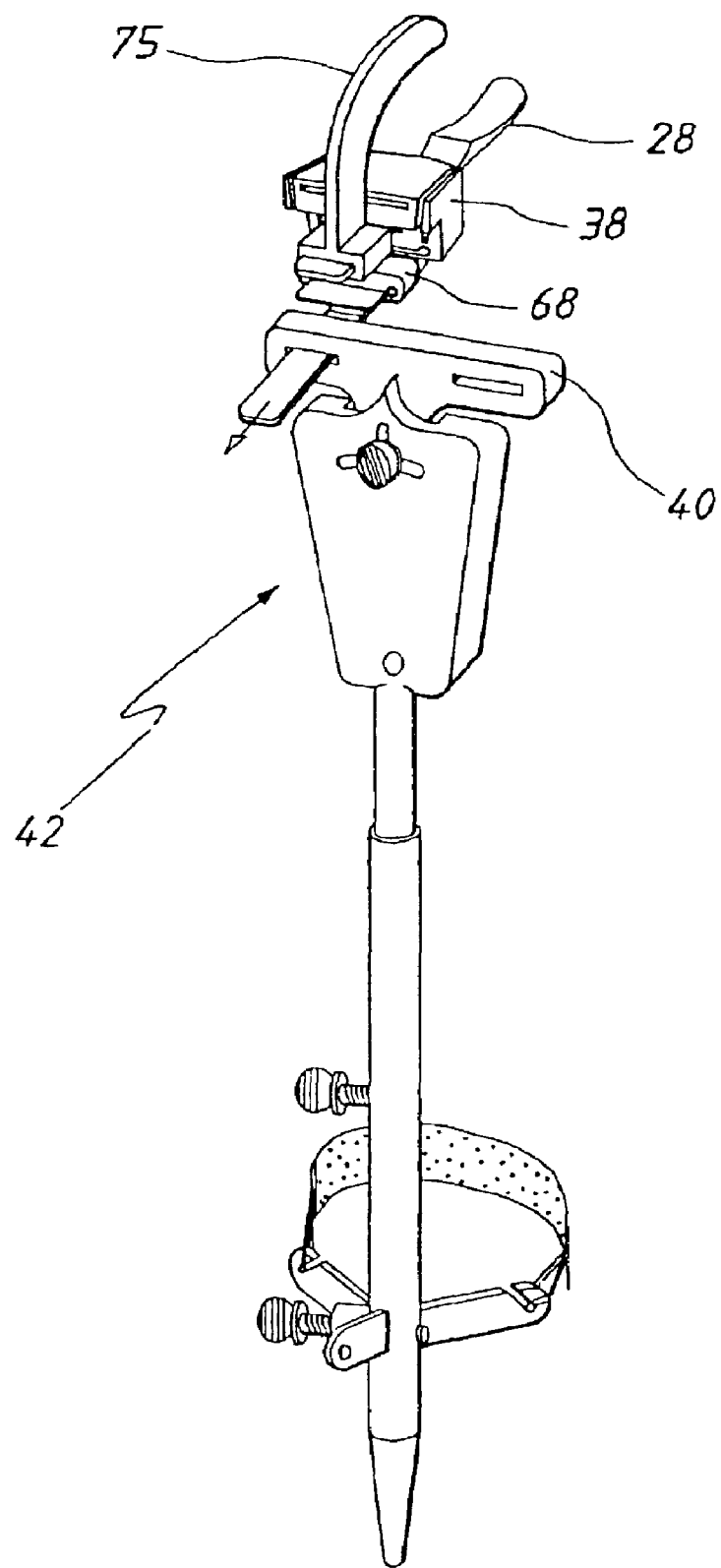
FIG. 9(a) is a perspective view of the apparatus of FIG. 8 when assembled.
Figure 9B:
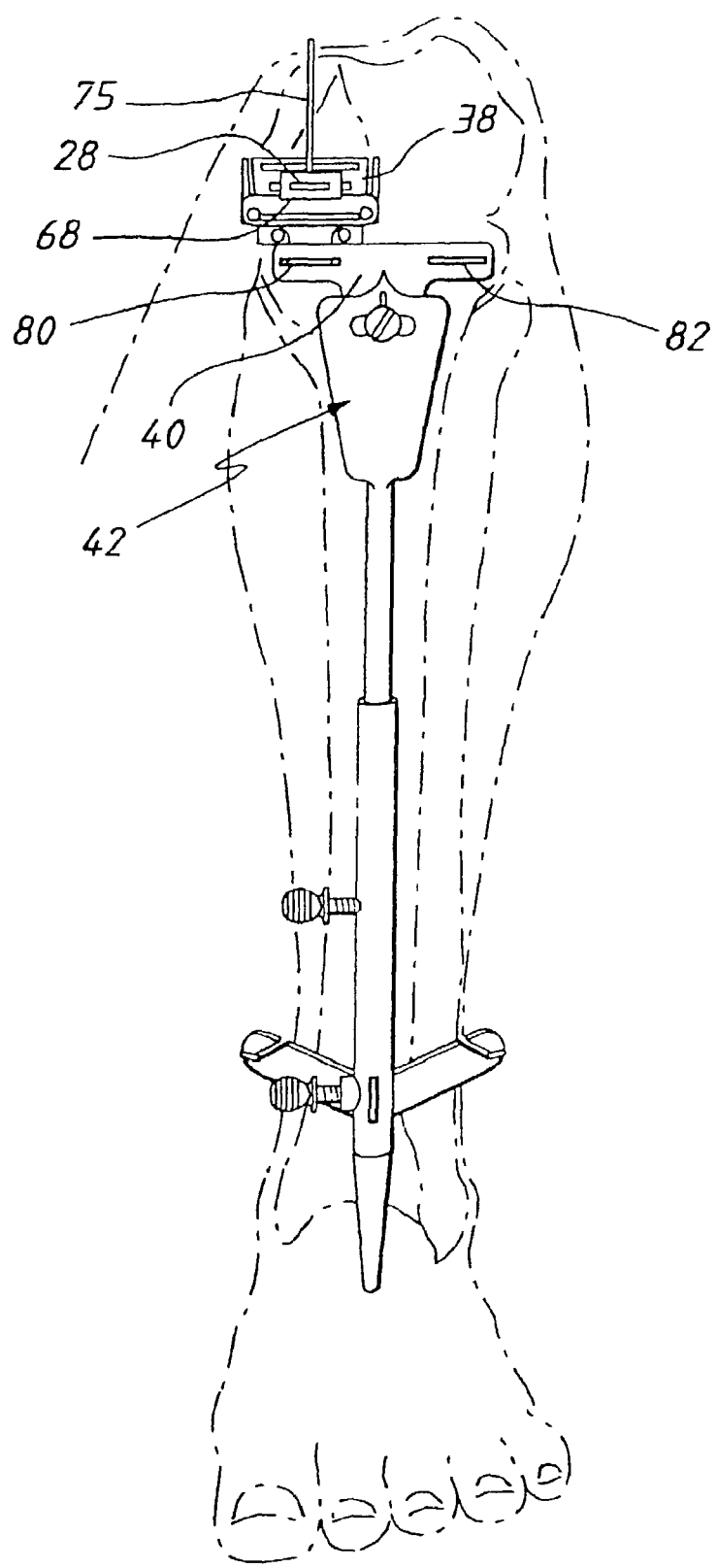
FIG. 9(b) is a diagrammatic front view of the apparatus of FIG. 8 fitted to the leg of a patient.

The apparatus when assembled is shown in FIG. 9(a) and when secured in position about the knee joint in FIG. 9(b). As can be seen, the apparatus further incorporates a stylus 75 for assisting alignment of the cutting block with the femur and which is mounted on the protruding end of the spacer 28.

As shown in FIG. 11, the alignment component consists of a body 74 incorporating a forwardly projecting tongue 76 which lies in the same plane as rearwardly projecting tongue 66 and overlies a long tongue 78 of the body provided for insertion into slot 80 or 82 of the mounting platform 40 of the tibial alignment guide 42. The plane in which the forward and rearward tongues 76 and 66 lie extends at an angle φ relative to the long tongue 78 such that tongue 76 diverges from the long tongue 78 with distance along the long tongue.

Accordingly, the cutting block 38 when mounted on the alignment component and assembled with the tibial alignment guide 42 is orientated for guiding resection of bone at a downward angle of φ in the anterior to posterior direction of the knee joint. Typically, angle φ will be 3° although different alignment components may be provided in which angle φ differs from one to the next to allow selection of the most appropriate one for each patient. Alternatively, an alignment component may be utilised in which the tongues 66 and 76 lie substantially parallel with the long tongue 78 in the case where it is desirable for the tibia to be cut in a substantially horizontal plane of the tibia.

As will be appreciated, the slots 80 and 82 of the mounting platform 40 of the tibial alignment guide are spaced apart from each other along the mounting platform for allowing the cutting block 38 to be positioned adjacent to the lateral and medial condyles of either the right or left tibiae, respectively.

Once the cutting block is secured to the tibia as will be described further below, the alignment component 68 and the tibial alignment guide 42 are removed from about the knee joint without disturbing the cutting block and spacer assembly. This leaves lower guide slot 72 of the cutting block vacant for reception of a saw and subsequently guiding cutting of the medial condyle of the tibia in the resection of bone for fitting of the tibial prosthesis. The resection of bone from the tibia and the femur is performed while the knee is placed in about 90° to about 100° of flexion.

In this position, the top slot 60 of the cutting block 38 guides the saw for cutting of a posterior chamfer from the femoral condyle for fitting of the femoral prosthesis and as such, both the tibia and the femur are cut in a plane extending in the medial to lateral direction, respectively.

Figure 12:
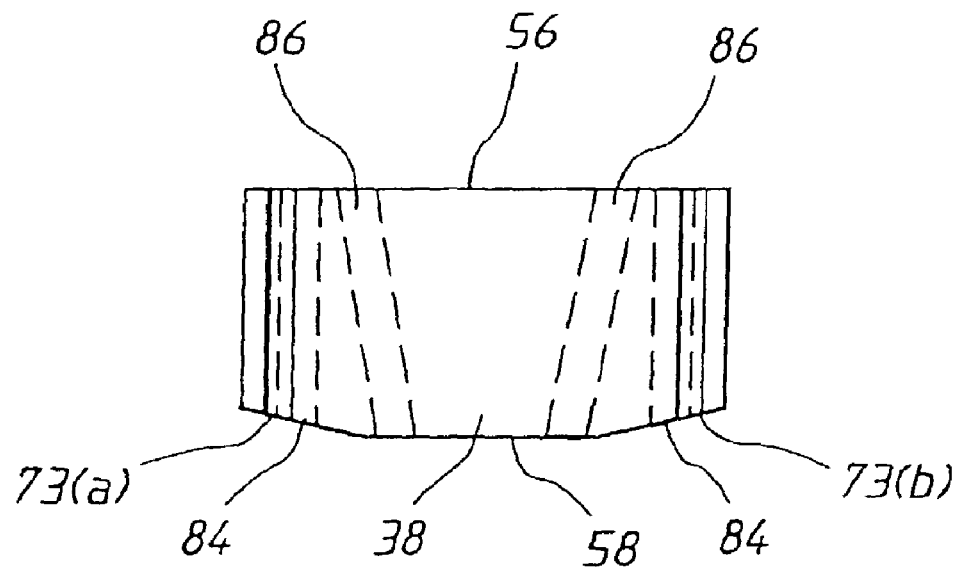
FIG. 12 is a schematic plan view of the guide jig of FIG. 10 indicating the orientation of channels defined in the jig for reception of pins for securing the jig in position about the knee joint.

Channels 84 and 86 are provided in the cutting block for reception of trocar pins 88 for securing the cutting block to the tibia. As shown schematically in FIG. 12, the bottom channels 86 converge toward each other in the front to the rear direction of the cutting block and are obliquely orientated with respect to the top pair of channels 84. Apertures 90 defined in the alignment component 68 are positioned to align with channels 84 of the cutting block when the cutting block is mounted on the tibial alignment guide to thereby hold the cutting block and alignment component together upon trocar pins being inserted therethrough into the tibia. In this way, the alignment component can be slid off the free end of the trocar pins leaving the cutting block behind in position about the knee joint.

Figure 13:
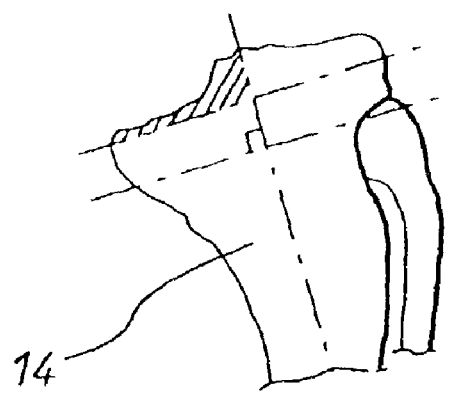
FIG. 13 is a diagrammatic partial view of a tibial shaft.

In the case of bowed varus tibiae, the cutting block will be arranged substantially perpendicular with respect to the metaphyseal axis of the tibial shaft as indicated in FIG. 13.

Figure 14:
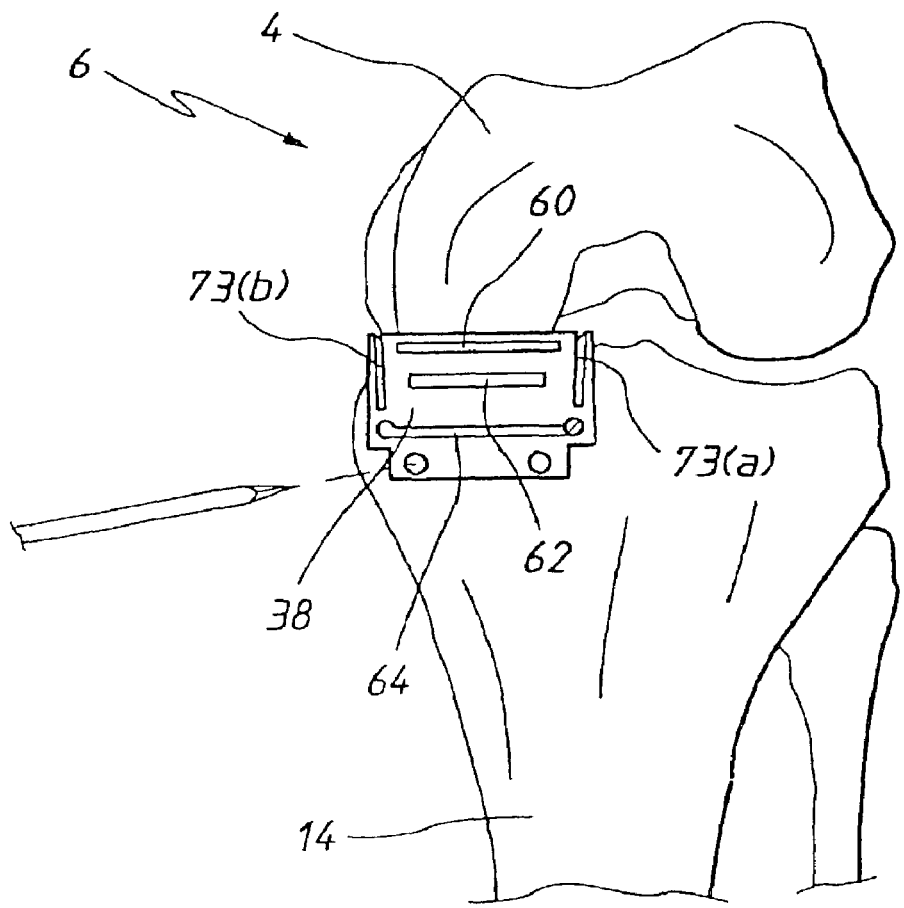
FIG. 14 is a diagrammatic front view of the guide jig fitted in position about the knee joint.
Figure 15:
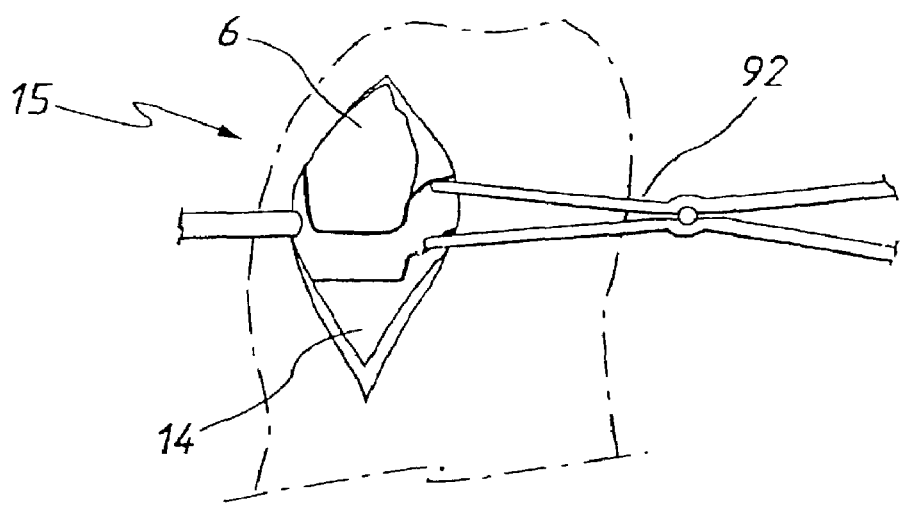
FIG. 15 is a front diagrammatic view showing the medial condyles of the femur and the tibia following resection thereof.

FIG. 14 illustrates the positioning of the cutting block 38 for the resection of the medial condyles of the tibia and femur while the tibia is placed in flexion with respect to the femur, and with the alignment component 68 and tibial alignment guide 42 removed. Once the transverse cuts to the tibia and the femur have been performed, a downwardly directed cut into the tibia guided by the relevant one of channel 73(a) or 73(b) of the cutting block is performed for removal of a segment of bone from the tibia to form a recess therein. The cutting block 38 and spacer 28 assembly is then removed to allow the downwardly directed cut into the tibia to be completed. At this time, any remaining posterior osteophytes and meniscus are also removed as required. The resected medial condyles of the tibia and femur following removal of the cutting block and spacer assembly is shown in FIG. 15. The use of a knee joint spreader 92 to maintain suitable access to the knee joint space is also shown. Alternatively, a suitable retractor may be utilised.

Figure 16:
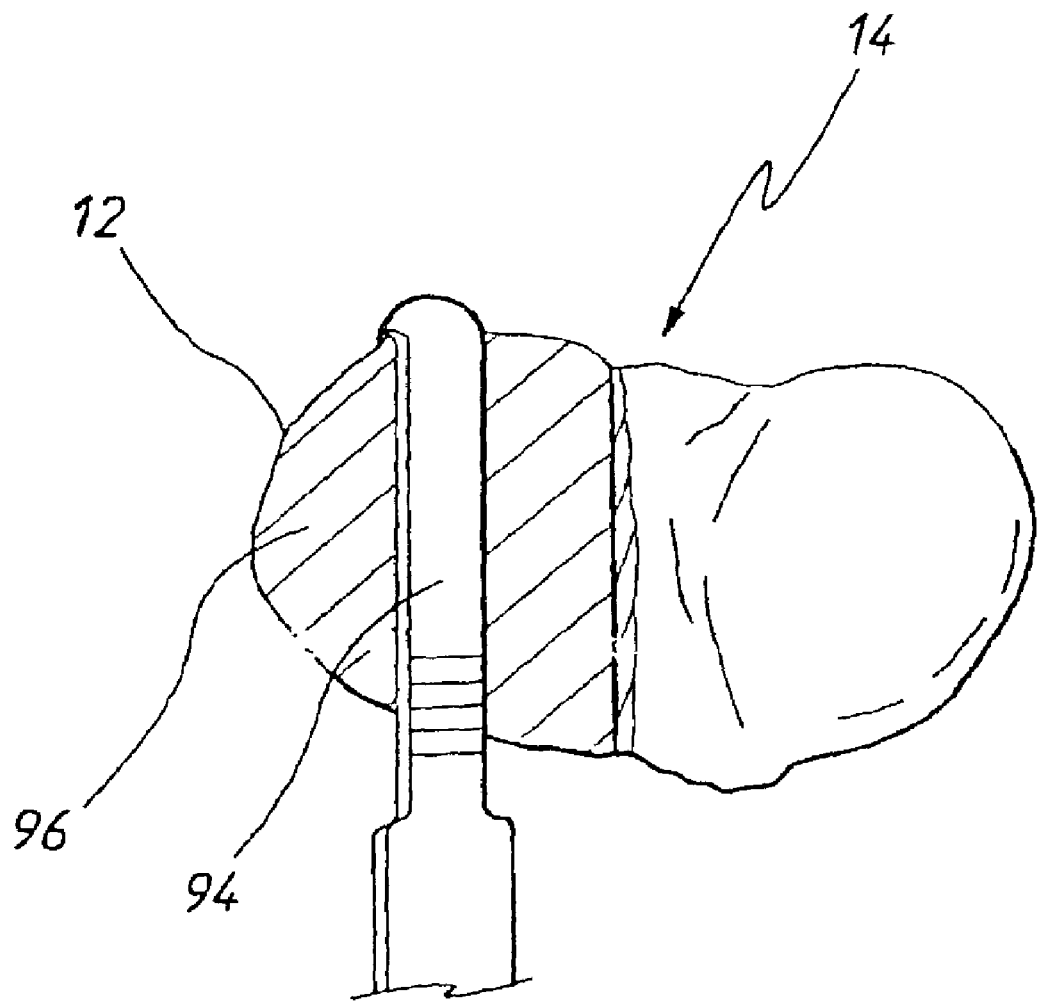
FIG. 16 is a diagrammatic view illustrating the use of a tibial sizing device for determination of an appropriate size of tibial implant.
Figure 17:
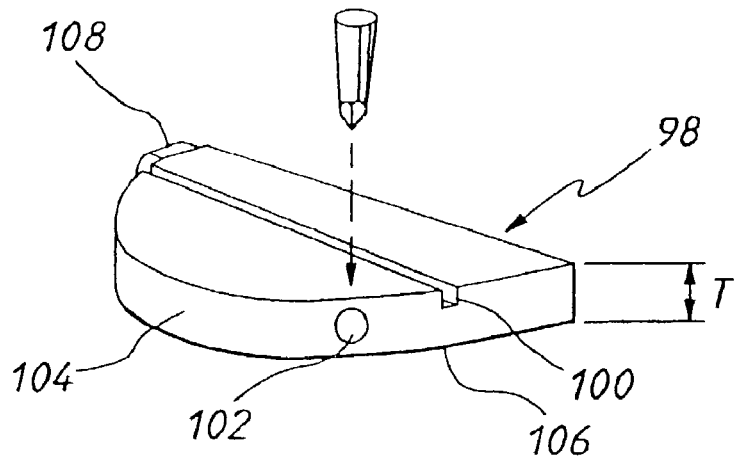
FIG. 17 is a perspective view of a tibial trial.

A diagrammatic plan view of the resected tibia is shown in FIG. 16. As indicated, following resection of the tibia, a tibial sizing device 94 is used to check the anteroposterior dimension of the resected tibial surface 96 for selection of an appropriately sized tibial trial 98 for being pinned into position on the resected surface. An example of a suitable tibial trial is illustrated in FIG. 17.

The profile of the tibial trial 98 and its thickness T match that of the tibial prosthesis 10. As will be appreciated, and with reference to FIG. 16, the profile of both the tibial trial 98 and tibial prosthesis 10 substantially match the profile of the resected tibial surface 96 of the tibia.

Figure 18:
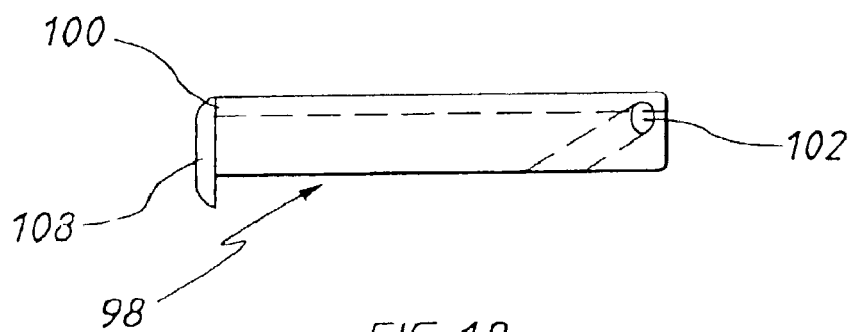
FIG. 18 is a diagrammatic view of the tibial trial of FIG. 17.

A channel in the form of a guide groove 100 is defined across the tibial trial for being orientated in the anteroposterior direction when the tibial trial is fitted in position. An obliquely orientated channel 102 extends from the side face 104 of the tibial trial through to its base 106 for reception of a pin therein for securing the tibial trial to the tibia. A tab 108 on the posterior side of the tibial trial depends from the base 106 as is more clearly shown in the diagrammatic size view of the tibial trial shown in FIG. 18, for assisting positioning of the tibial trial on the resected surface of the tibia.

Figure 19:
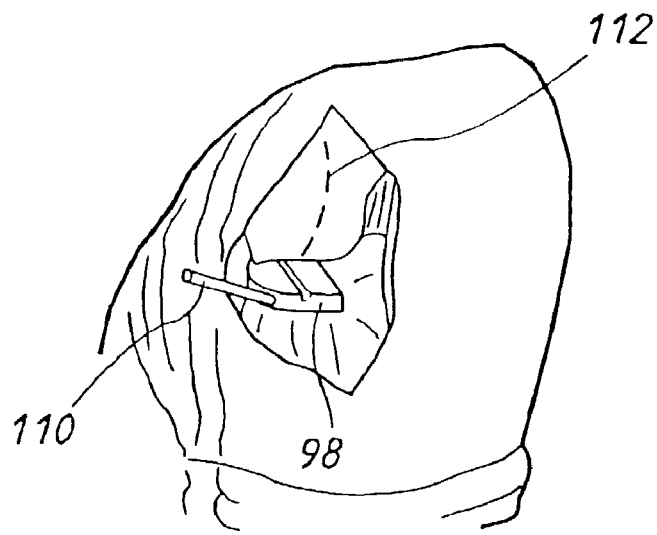
FIG. 19 is a diagrammatic anterior view of the tibial implant of FIG. 16 fixed in position on the tibia of the knee joint.

The tibial trial when secured in position on the resected tibial surface 96 of the tibia by pin 110 is shown in FIG. 19. To accommodate the upstanding central fin 16 of the femoral prosthesis 2, a reciprocating saw blade is located along the guide groove 100 of the tibial trial and the tibia moved about the femur through an arc of motion to cut a channel into the femur indicated by dotted line 112. In this way, the groove 100 of the tibial trial determines the correct orientation for fitting of the femoral prosthesis on the femur.

As an alternative, rather than cutting the channel into the femur as described above, a marker pen or diathermy can be used in place of the saw blade for marking of the femoral condyle for subsequent cutting of the channel into the femur using a saw blade in a free hand manner.

Figure 20:
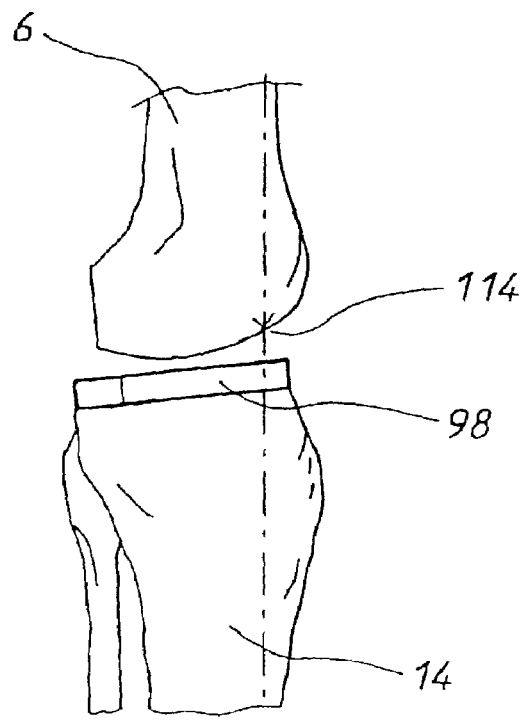
FIGS. 20 and 21 are diagrammatic views illustrating marking of a femoral condyle of the knee joint for further resection of the femur to enable fitting of the femoral prosthesis of FIG. 3.
Figure 21:
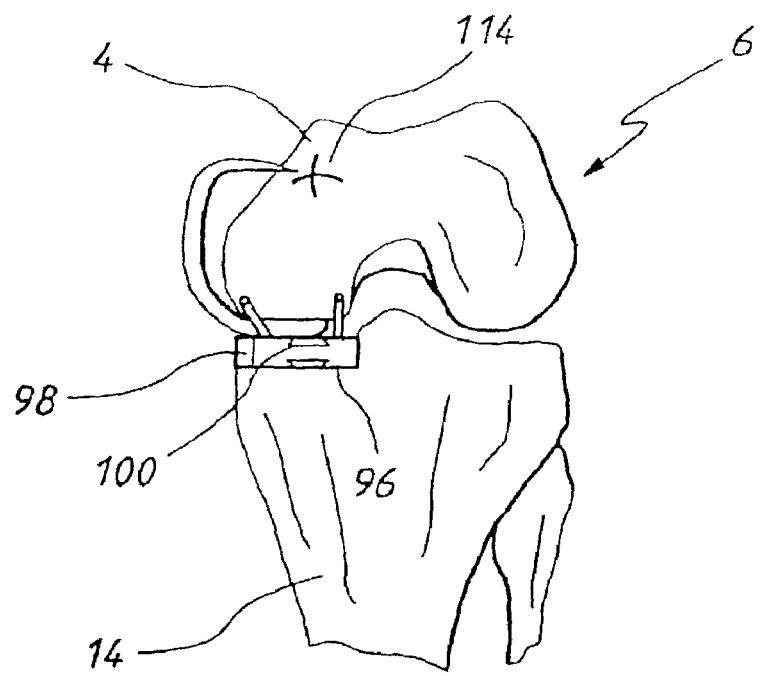

With the knee in full extension, and with care being taken not to hyperextend the knee, an imaginary line aligned with the groove 100 of the tibial trial is projected from the anterior side of the tibial trial 98 to the corresponding femoral medial condyle as indicated in FIG. 20. The point 114 at which the line strikes the femur is marked and corresponds to the optimal position of the anterior edge 116 of the femoral prosthesis 2, and is indicated more clearly in FIG. 21 where the tibia is shown in flexion relative to the femur.

Figure 22:
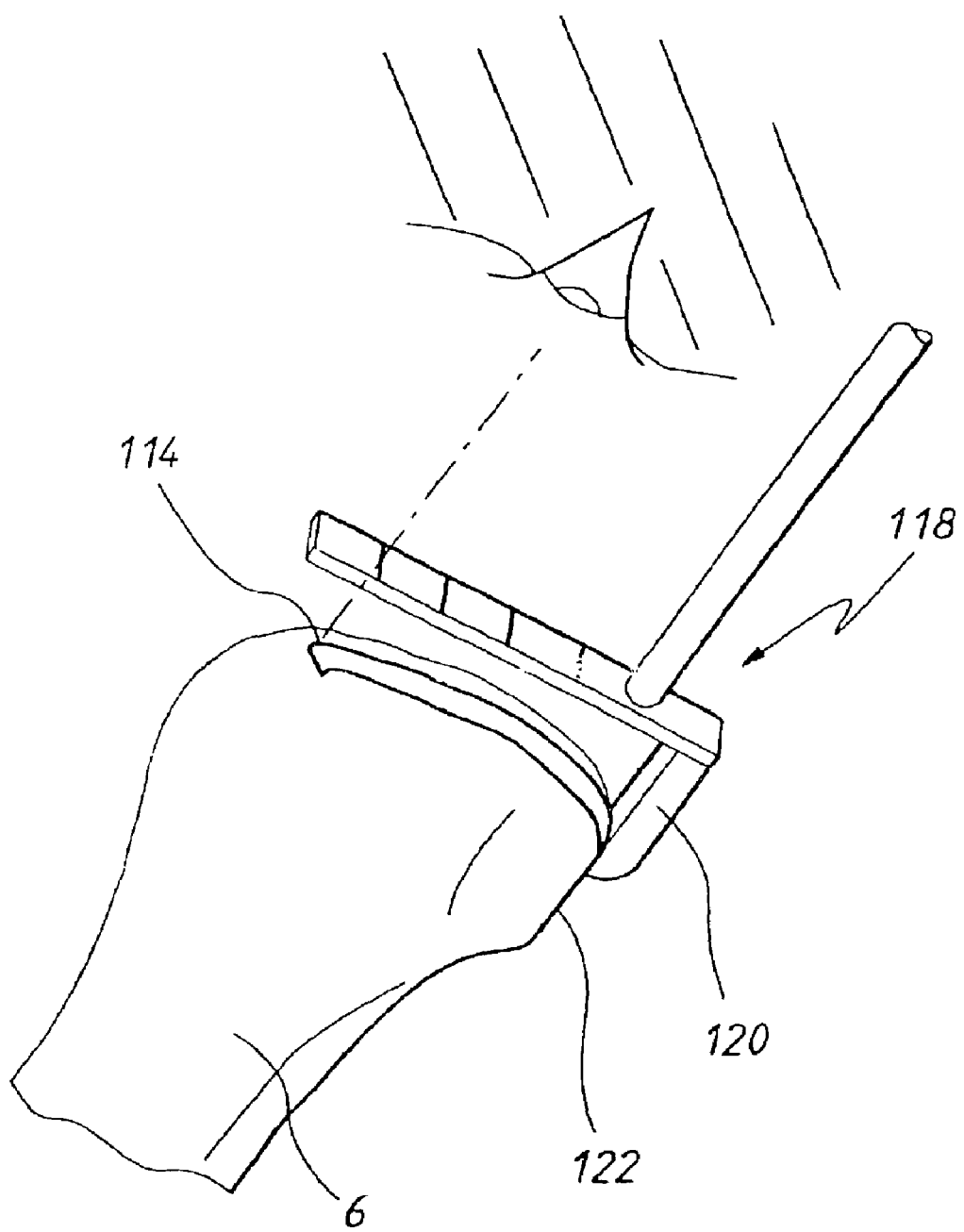
FIG. 22 is a diagrammatic view illustrating the use of a femoral sizer for determination of the appropriate sized femoral prosthesis.

A femoral sizer 118 is then aligned with the channel cut into the femur, with the posterior end 120 of the femoral sizer positioned flushly against the resected posterior face 122 of the femoral condyle, to allow determination of the required size of femoral prosthesis 2 by comparing the position of the mark 114 with calibrated markings on the femoral sizer as shown in FIG. 22.

Figure 23:
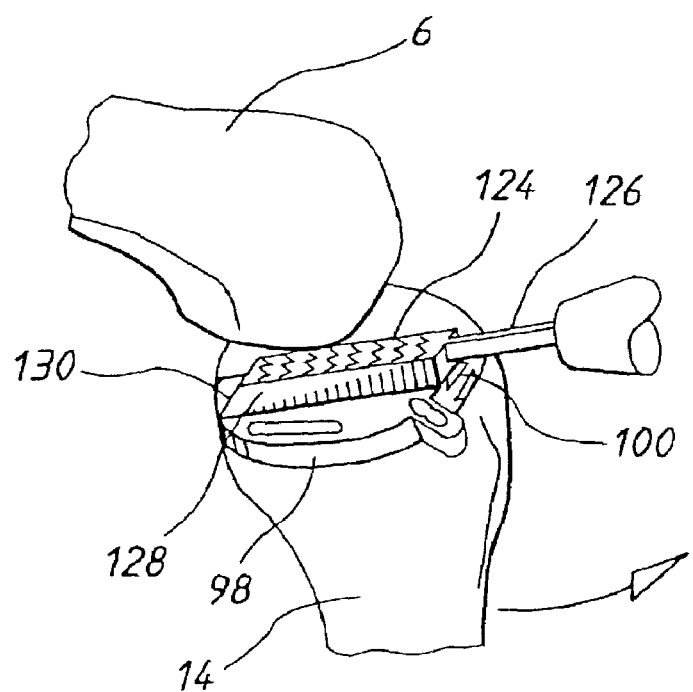
FIG. 23 is a diagrammatic view illustrating the use of a femoral shaping rasp for shaving bone from the relevant condyle of the femur to enable fitting of the femoral prosthesis.

The femoral condyle can then be sculpted as required to accommodate the fitting of the femoral prosthesis 2. This can be readily achieved with the use of a cutter device such as a femoral shaping rasp 124 illustrated in FIG. 23 or for instance, a router having a rotatable cutter for resecting bone from the femur. As can be seen, the rasp 124 has a tang 126 for being received by a reciprocating power saw. The body 128 of the rasp is generally flat and is provided with a tapered leading end 130. A key (not shown) extends centrally along the base of the rasp for reception in the guide groove 100 of the tibial trial 98. Accordingly, the groove of the tibial trial 98 acts to guide the reciprocating motion of the rasp when positioned on the tibial trial under the femur as illustrated in FIG. 23.

As will be understood, to sculpt the femur, the tibia is rotated about the femur through an arc of motion between forward and backward positions during which movement the cutting face of the rasp acts to progressively shave away the required thickness of the femur. It will also be appreciated that the thickness of the rasp is such to ensure that the original spacing between the femur and the tibia provided by the selected spacer 28 will be essentially retained upon the femoral prosthesis being fitted, for substantially maintaining the optimised balance in ligaments and other soft tissue initially provided by the spacing of the femur from the tibia by the selected spacer.

Figure 24:
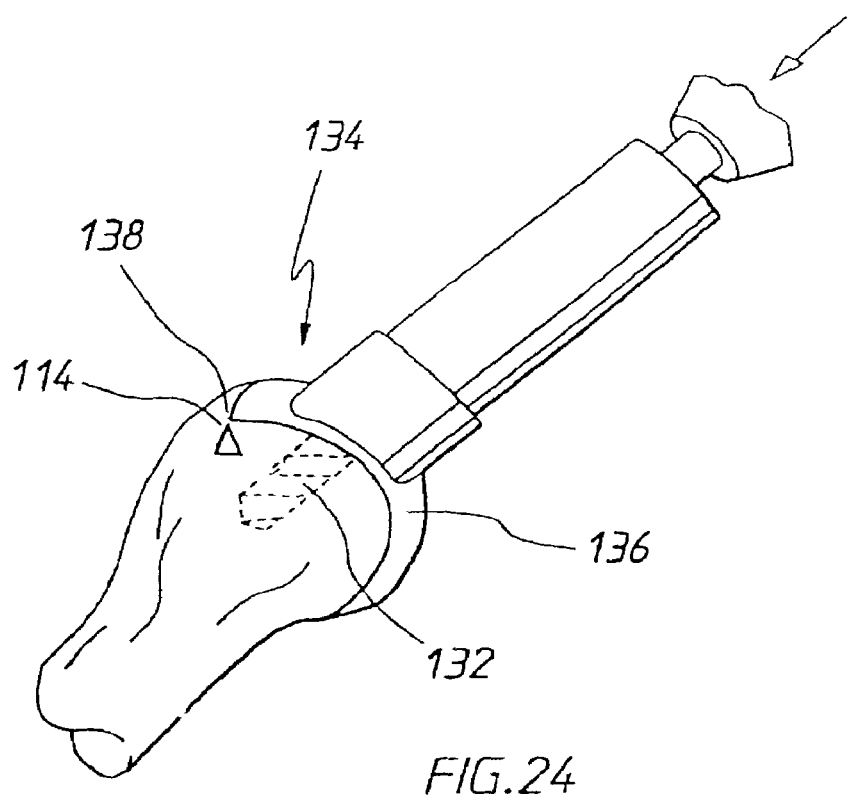
FIG. 24 is a diagrammatic view illustrating the use of a femoral peg drill guide to drill bore into the femur for reception of the femoral peg of the femoral prosthesis shown in FIG. 3.

Drilling of the required bore 132 into the femur for reception of the peg 18 of the femoral prosthesis is readily achieved using a femoral peg drill guide 134 carrying a guide bracket 136 having a corresponding shape to the femoral prosthesis. Determination of the position for drilling the bore 132 is achieved by aligning the anterior tip 138 of the guide bracket 136 over the location 114 determined on the femur to correspond with the optimal positioning of the anterior end of the femoral prosthesis and reference is drawn to FIG. 24 for explanatory purposes.

Subsequently, the joint space is lavaged and a femoral trial affixed to the femur for a final assessment of joint stability and joint kinematics.

The tibial and femoral trials are then removed and the joint space thoroughly cleaned using pulsatile lavage prior to the tibial prosthesis 10 and the femoral prosthesis 2 being fixed to the tibia and the femur respectively, using appropriate conventionally known bonding cement such as polymethylacrylate bone cement. Prior to closing the wound the joint space is again thoroughly lavaged and if deemed necessary, local anaesthetic may be infiltrated at the wound site to assist post operative pain relief.

As will be appreciated, the tibial prosthesis used in a method as described herein may be selected from a number of such prostheses with a different thickness T to each other. The selected prosthesis will of course depend on the thickness of the spacer 28 required to initially optimise tension and balance in the action of the relevant ligaments and soft tissue structures of the knee joint during the movement of the tibia about the femur between forward and backward positions. For each thickness of tibial prosthesis, a corresponding cutting block 38 for guiding cutting of the tibia and the femur at the required spacing to accommodate the selected tibial prosthesis will be provided. Alternatively, a cutting block able to be adjusted to alter the spacing between the guide slots 60 and 62 as necessary to correspond to the thickness T of the selected tibial prosthesis may be used.

Figure 25:
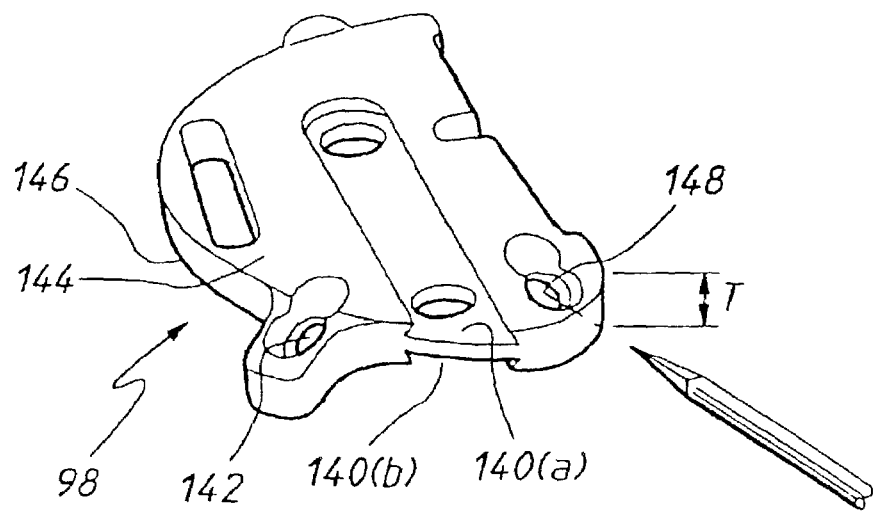
FIG. 25 is a perspective view of a tibial implant of the invention.
Figure 26:
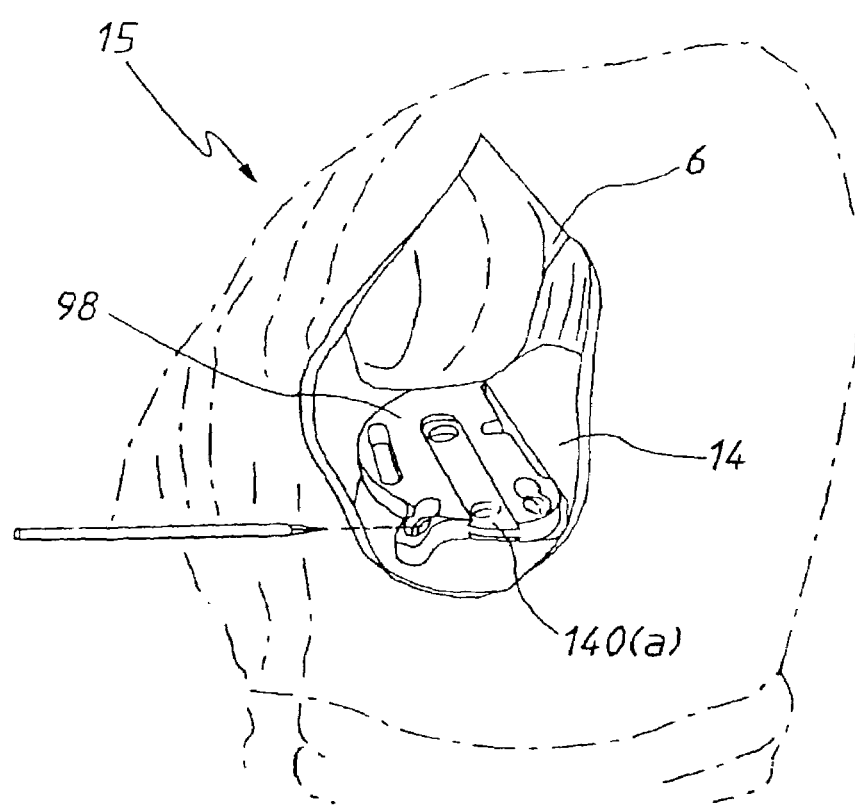
FIG. 26 is a diagrammatic view of the tibial implant of FIG. 25 fixed in position on the tibia.

Another embodiment of a tibial trial 98 having a guide channel 140(a) extending part way across the tibial trial in a generally anteroposterior direction is shown in FIG. 25 for reception of a router. The channel 140(a) has a dove tailed cross-section lying in a plane extending perpendicularly with respect to the major axis of the tibial trial. An identical channel 140(b) is defined in the underside of the tibial trial. As can be seen, this tibial trial is again provided with a channel 142 which extends from the upperside face 140 of the tibial trial through to its base 146 for reception of an obliquely orientated trocar pin therein for securing the tibial trial to the tibia. A further channel 148 is defined on the opposite side of the tibial trial for reception of an obliquely directed trocar pin. Indeed, the tibial trial is designed such that the tibial trial may be secured to either the medial condyle or the lateral condyle following the resection of bone therefrom. That is, by simply rotating the tibial trial 180° about its major axis the trial can be pinned to either medial lateral resected surfaces 96 of the tibia by the insertion of trocar pins through channels 142 and 148. The tibial trial when secured in position on the tibia prior to receiving the router is shown in FIG. 26.

Figure 27A:
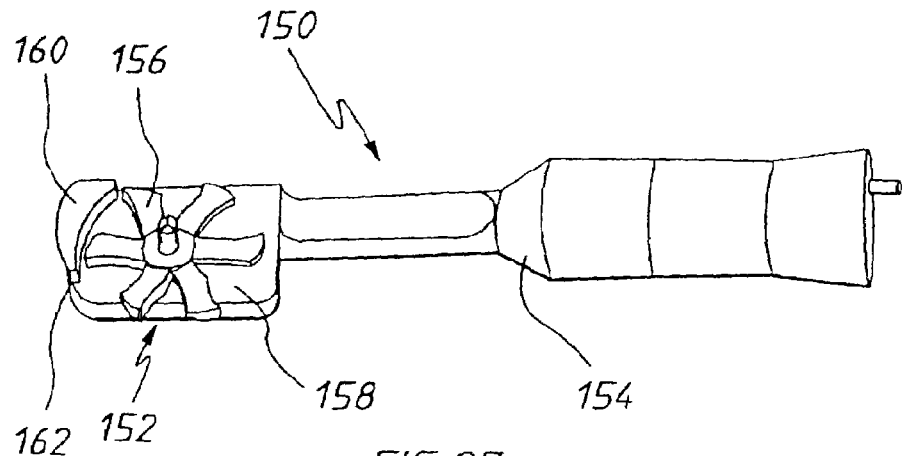
FIG. 27(a) is an elevated side view of a cutting device for resecting bone from the femur.
Figure 28:
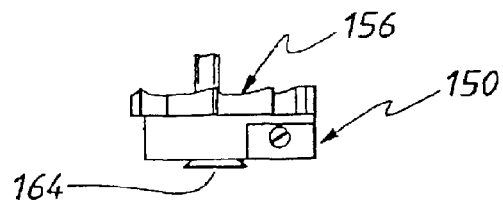
FIG. 28 is an end view of the cutting device of FIG. 27(a)
Figure 29:
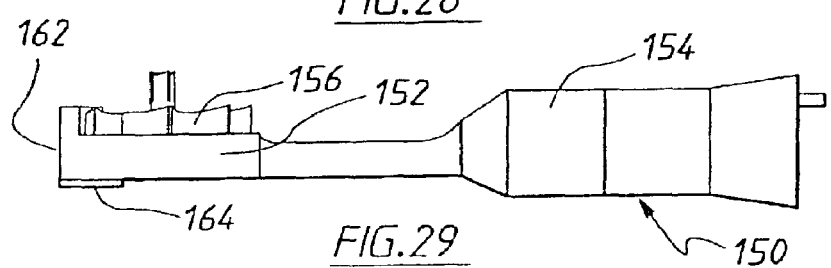
FIG. 29 is a side view of the cutting device of FIG. 27(a)

The router 150 shown in FIG. 27(a) comprises a flat head 152 having a substantially constant thickness along its length and which is detachably connected to body 154 of the router. A cutter disk 156 is seated in an aperture defined in the upperside 158 of the router head 152. A forward guard 160 is defined on the leading end 162 of the router. An end view of the router is shown in FIG. 28 and a side view in FIG. 29. As can be seen, a boss 164 having a dove tailed profile corresponding to that of the guide channel 140(a) of the tibial trial of FIG. 25 depends from the underside of the router 150 for reception in the guide channel 140(a) for thereby inhibiting lifting of the router from the tibial trial.

Figure 27B:
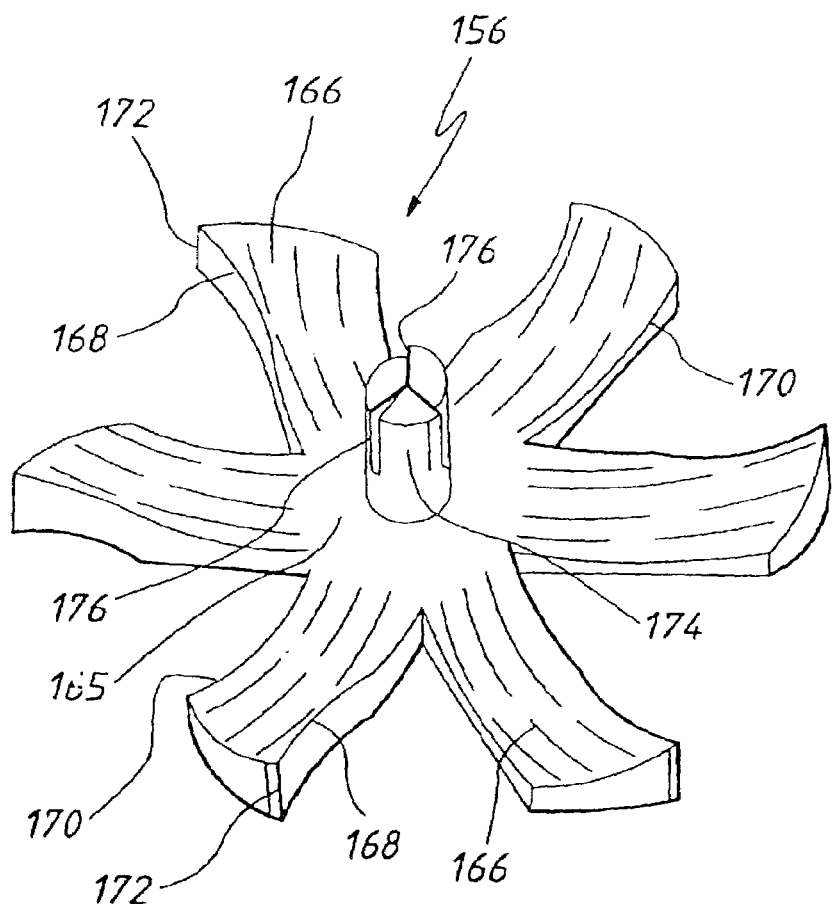
FIG. 27(b) is a perspective view of the cutter blade disk of the cutting device of FIG. 27(a)

The cutter disk 156 is more clearly shown in FIG. 27(b) and has a dished upper surface 165 and a plurality of radially directed blades 166. Each blade decreases in thickness from a leading cutting edge 168 to a trailing edge 170. A further cutting edge 172 is defined at the outer peripheral end of each blade. In addition, an integrally formed upstanding cutting blade 174 is centrally located on the cutter disk. The upstanding blade 174 has a plurality of upwardly directed cutting edges 176 spaced at 120° intervals around the blade. Specifically, the cutting edges 176 are defined on both the side and top end of the upstanding blade as can be seen.

Figure 30A:
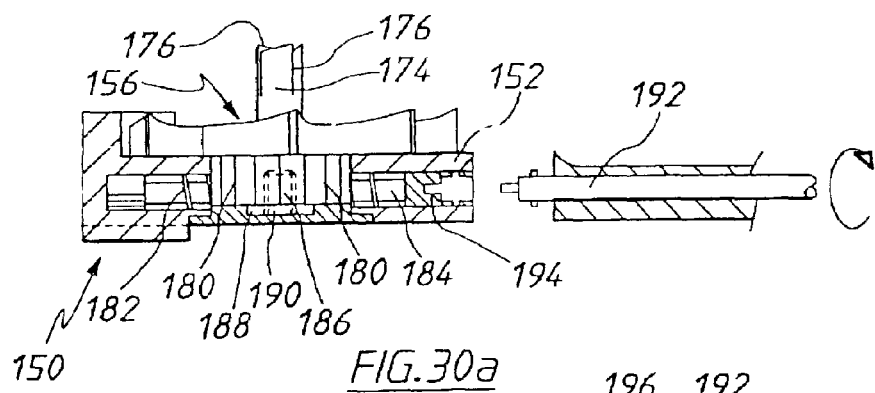
FIG. 30(a) is a longitudinal cross-sectional view of the cutting device of FIG. 27(a)

Turning now to FIG. 30(a), the cutter disk 156 further incorporates an integrally formed drive gear with a plurality of vertically orientated teeth 180 which mesh with the screw of the screw drive 182 rotatably received within the head 152 of the router 150.

The cutter disk 156 has an internal female thread which mates with a screw 186 extending through collet 188 received in recess 190 defined in the underside of the router head, such that the cutter disk 156 is thereby retained in position on the router head and is rotatable with respect to the router head.

Figure 30B:
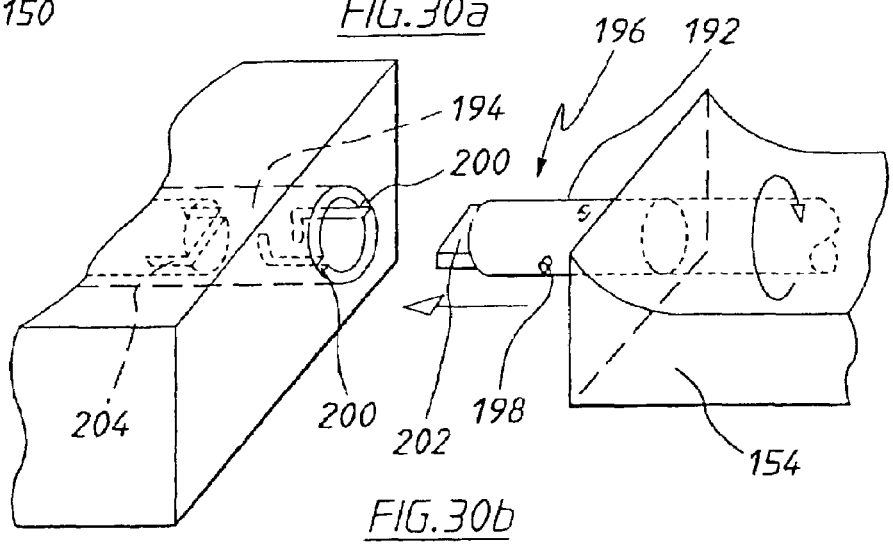
FIG. 30(b) is a diagrammatic partial view of a coupling arrangement used for coupling the head and body of the cutter device of FIG. 27(a) together.

A drive shaft 192 is rotatably mounted within the router body and projects therefrom for engagement with the female bayonet coupling 194 of the screw drive 184 of the router head. As shown in FIG. 30(b), the projecting end 196 of the drive shaft 192 carries bayonet pin 198 for reception in the bayonet recesses 200 of the bayonet coupling for thereby locking the router head 152 to the router body 154. The projecting end 196 of the drive shaft 192 is further provided with a flat drive projection 202 which slots into the slot 204 of the bayonet coupling for driving rotation of the screw drive 184 and so causing rotation of the cutter disk 156. The router body is adapted for being coupled with a power drive for driving rotation of the cutter disk typically in the range of from 5,000 rpm to about 7,000 rpm. As will be understood, once used, the router head 152 may be removed and discarded. Desirably, however, the body 154 of the router is sealed and is reusable following sterilisation.

Rather than engaging the cutter disk directly, the screw drive 184 of other embodiments may be arranged to drive a gear arrangement comprising a single gear or for instance a gear train incorporating a number of gears for driving the cutter disk. Alternatively, the router may incorporate a drive in the form of an endless belt, band or the like which upon being driven by the drive shaft causes rotation of the cutter disk.

As indicated above, the cutter disk 156 is freely rotatable with respect to the head of the router and may be lifted from the head upon the screw 186 being removed to allow replacement of the cutter disk with another of the same or different design. A blunt cutter disk may result in thermal necrosis of bone of the femur and accordingly it is desirable to replace the cutter disk if necessary. To assist in the insertion of the router into the knee joint, the leading end 162 of the head of the router has an arcuate profile.

Figure 31:
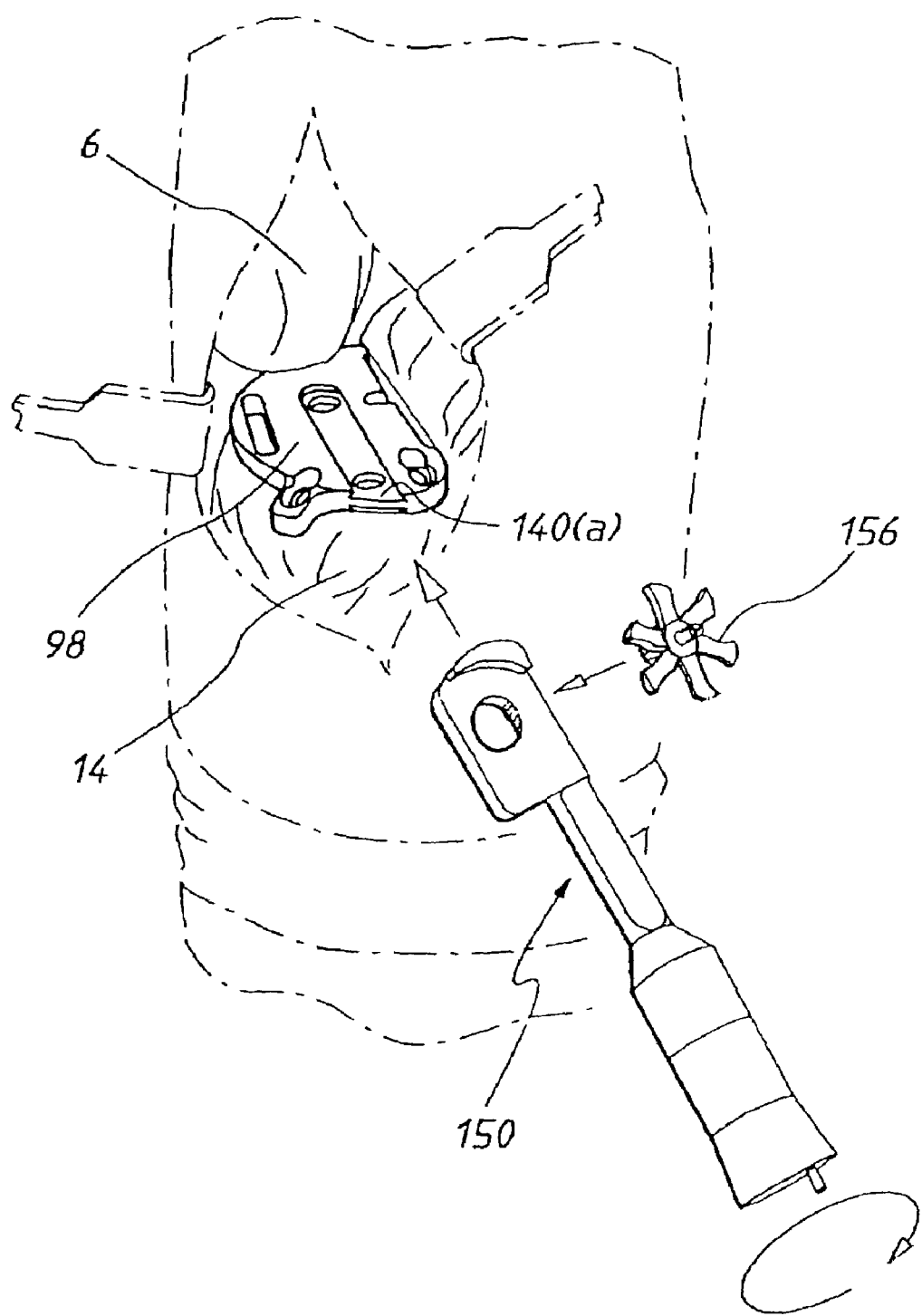
FIGS. 31 and 32 illustrate reception of the cutting device of FIG. 27(a) the tibial implant of FIG. 25 in unicondylar arthroplasty.
Figure 32:
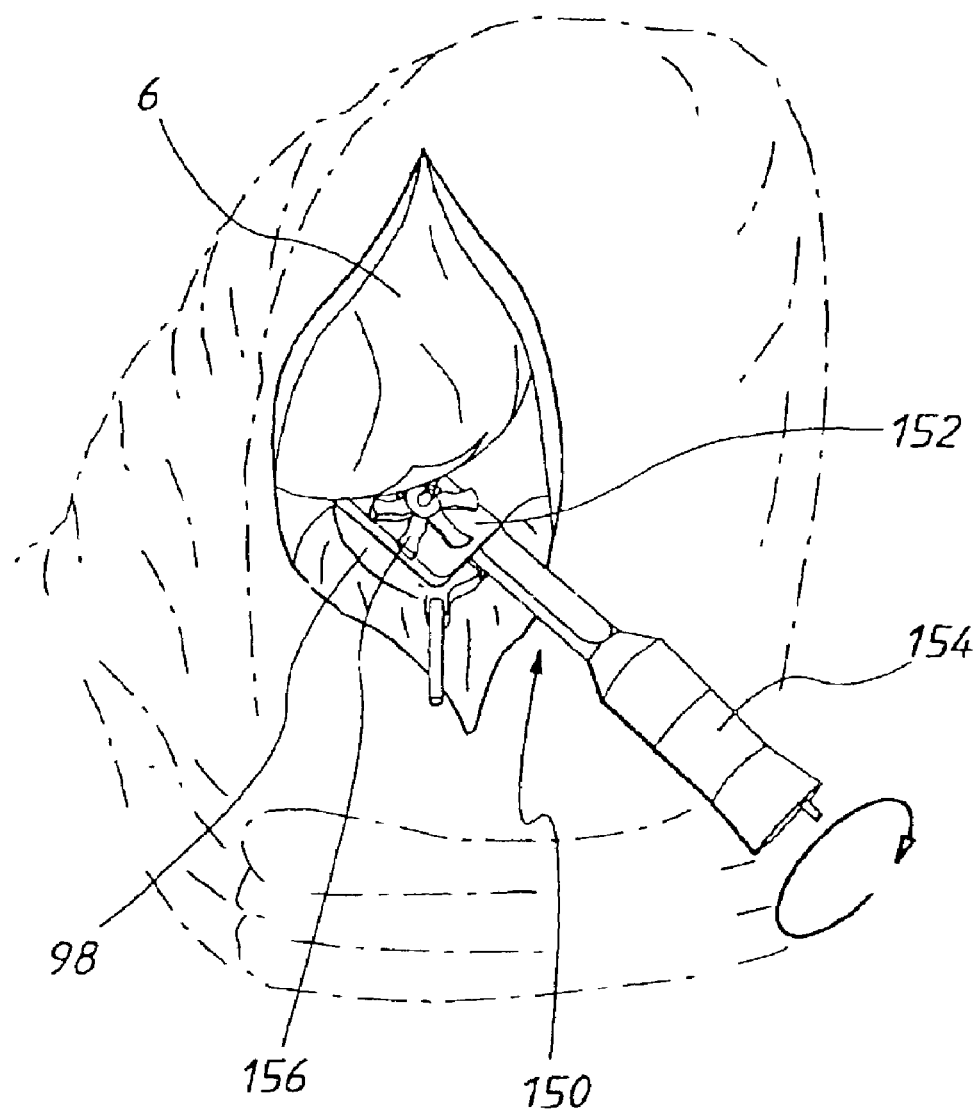

The insertion of the router into the knee joint is indicated in FIGS. 31 and 32, and the use of the tibial trial of FIG. 26 and router 150 in unicondylar knee arthroplasty is illustrated in FIGS. 33(*a*) to 33(*c*). Specifically, the tibia is again placed in flexion with respect to the femur, and the boss 164 of the router is inserted into the guide channel 140(*a*) of the tibial trial as shown in FIG. 32. Upon operation of the router and the tibia being moved about the femur through an arc of motion to an extended position, bone is resected from the femur to the desired depth in the direction of movement of the tibia as shown in FIG. 33(*b*). As indicated more clearly in FIG. 33(*c*), the channel 206 for reception of the central fin 16 of the femoral prostheses is simultaneously cut into the femoral condyle by upstanding blade 174 of the cutter disk 156 of the router 150.

Rather than cutting the channel 206 for reception of the central fin of the femoral prosthesis simultaneously with the resurfacing of the femur utilising the cutter disk 156, the resurfacing of the femur and the cutting of the channel 206 may be achieved in a two stage process. That is, a cutter blade may be located in the router for cutting the channel in an initial step, and then that cutter blade replaced with one for resecting the required thickness of one from the femur and which incorporates an upstanding centrally located non-cutting boss for reception in the cut channel 206 to thereby guide the resurfacing of the femur. In this instance, the boss will generally be of a height such that a space remains between the upper end of the boss and the overlying roof of the channel.

Similarly, rather than resecting the posterior chamfer from the femur with a reciprocating saw utilising the cutting block 38 for guidance, the posterior chamfer may be resected from the femur with the use of a router 150 in which the router head 152 is provided without a guard 160. As such, a cutting block may be provided that while being capable of being coupled with the spacer selected for optimum spacing of the femur from the tibia as described above, may only be adapted for guiding cutting of the tibia at the relevant depth therein and not the femur.

While the method has been described in relation to arthroplasty performed on the medial condyles of the tibia and the femur, unicondylar arthroplasty may be performed on the lateral condyles in the same manner.

In addition, rather than removing the entire upper segment of the relevant condyle of the tibia in unicondylar arthroplasty to provide an exposed recess on which the tibial trial and subsequently the final tibial prosthesis 10 is onset and fixed in position as described above, a recess may be formed in the condyle into which the tibial trial and ultimately the tibial prosthesis are inset, respectively. An apparatus for providing such a recess in the tibia is shown in FIG. 34.

The apparatus comprises a router 208 and a guide jig 210 for guiding the router to form the inset recess 212, in this case in the medial condyle of the tibia 14.

The router 208 has an elongated body 214 housing a drive shaft 216 for driving rotation of a router blade 218 in the same manner as described for the router shown in FIG. 30, for resecting the bone from the tibia to the desired depth in the tibia. The drive shaft 216 projects from the trailing end 222 of the body 214 for reception by a power tool for driving rotation of the drive shaft.

A guide pin 224 projects from an underside of the router body 214 for reception in a recessed template 226 defined in the floor of channel 228 of the guide jig 210. A recessed area is also defined in the body of the router to allow the router to overlie the rim 232 of the recess and to allow the router blade to resect the bone from the tibia to the desired depth. The guide pin has a length to ensure reception in the recessed template of the guide jig when the router is positioned over the tibia prior to commencement of the resection of bone in the formation of the recess. Similarly, the depth of the recessed template is sufficient to ensure the entire exposed length of the guide pin is able to be accommodated therein.

The profile of the template 226 substantially matches the external profile of the tibial trial to be used, and the template is dimensioned for the recess to be of a size sufficient to allow the tibial trial to be seated on the resected tibial surface 96 at the base of the recess. Once received in the recess, the surrounding bone of the tibia acts to inhibit the tibial trial and subsequently the actual tibial prosthesis 10 from being transversely dislocated.

In order to position the guide jig 210 about the knee, the tibiofemoral cutting block 38 is firstly arranged adjacent to the tibia in the manner described above utilising the selected spacer 28 to determine the position of the cutting block with respect to the tibia, prior to the securing of the cutting block in position using trocar pins 234. As will be understood, trocar pins 234 are dimensioned for being inserted into the channels 84 and 90 of the cutting block and alignment component in a sliding fit and to allow the cutting block and alignment component 68 to be slid from the pins following resection of the one or both of the tibia and femur as described above.

Once the cutting block and spacer assembly has subsequently been slid from the trocar pins the guide jig 210 is slid onto the trocar pins 234 such that the trocar pins are received in longitudinally extending parallel channels 236 of the guide jig.

The router blade 218 projects from the head 220 of the router a distance such that when the router is received in the channel 228 of the guide jig, bone is able to be resected from the tibia to a depth corresponding to the position of the bottom 72 of the lower slot 64 of the cutting block 38 prior to removal of the cutting block from the tibia. Resection of bone from the tibia beyond this depth is inhibited by abutment of the underside surface 238 of the rear end region 240 of the router with the floor 242 of the channel of the guide jig. To resect bone from the tibia to greater depths to accommodate different sized tibial trials, different sized router blades may be utilised on the router.

In order to enhance stability, the guide jig is provided with a rest 244 that projects downwardly from the leading end 246 of the guide jig and which rests against the leg of the patient to thereby assist in maintaining the jig in position at the angle in the anterior to posterior direction determined by the alignment component 68. The guide jig is secured in position on the tibia by pin 248 inserted into the tibia through channel 250 defined in the rest 244 which channel extends at an oblique angle with respect to parallel channels 236 of the guide jig receiving trocar pins 234.

The recess 212 in the tibia is formed and shaped by the application of downward pressure to the router as the router is moved side to side and forward and backward in the guide jig, the movement of the router across the tibia being limited by the restricted field of movement of the guide pin in the recessed template of the jig. Accessible tibial osteophytes may be removed prior to or following the formation of the recess in the tibia. To allow for the resection of differently sized recesses, a range of guide jigs may be provided with templates of different width and length dimensions. Similarly, the location of the guide pin 224 on the router may be adjustable along the router to accommodate resection of the recess in the desired position on the tibia, or otherwise the guide jig may be adapted for facilitating adjustment of the position of the guide jig along the trocar pins. This may be achieved for instance by the rest being extendible relative to the remainder of the guide jig for causing the desired displacement of the template away from the knee joint.

The tibia trial when seated in the recess will typically protrude above the rim 232 of the recess. Usually, the tibial trial will be secured in position in the recess by an appropriately located pin inserted into the tibia at an oblique angle (not shown).

The channel for receiving the central fin 16 of the femoral prosthesis may then be cut into the corresponding condyle of the femur if not already achieved simultaneously during the resection of the femur with the use of a router of the type shown in FIG. 30.

Rather than utilising a guide jig arrangement of the type shown in FIG. 34 for resecting a channel into the tibia for insertion of a tibial trial and subsequently a tibial prosthesis therein, apparatus as shown in FIG. 8 may more desirably be utilised. In this instance, rather than the cutting block 38 being mounted on the rearward tongue 66 of the alignment component 68, the cutting block is rotated 180° and mounted on the forward tongue 76 of the alignment component as indicated in the exploded view shown in FIG. 35 and the view of the assembled arrangement indicated in FIG. 36. Accordingly, in this instance the alignment component 68 is located between the cutting block 38 and the tibia 14 for resection of the posterior chamfer from the femur 6 as indicated above. Once the posterior chamfer has been resected, the cutting block 38 is slid from the alignment component 68 leaving the alignment component 68 behind in position relative to the tibia.

The body 74 of the alignment component is dimensioned such that the upper surface 252 of the head 254 is aligned at the same level as the bottom of the middle slot 62 of the cutting block for the spacer, prior to the cutting block being slid from the trocar pins securing the alignment component in position relative to the tibia. The upper surface 252, therefore, may therefore be used as a rest for a router 256 as shown in FIG. 37 for removing bone from the tibia to form a recess to the desired depth for the seating therein of a tibial trial and thereafter the ultimate tibial prosthesis. That is, the height of the cutter blade 258 of the router 256 is dimensioned such that the floor of the recess resected into the tibia is at a level corresponding to the level of the bottom 72 of the lower slot 64 of the cutting block when located in position adjacent to the tibia. As with the cutter blade of the router shown in FIG. 30, the cutter blade 258 has cutting edges defined on both the sides and top end of the blade.

The correct size of the recess to be resected is firstly ascertained by locating different tibial trial templates on the tibial condyle and selecting the most appropriate one prior to marking the profile of the selected templated on the tibial trial in the required location with methylene blue or other suitable dye as is conventionally known in the art.

Following removal of the alignment component 68 for insetting of the tibial trial in the resected recess, the femur may be further resected as described above for the fitting of the femoral prosthesis.

Another router employing a cutter disk 260 is shown in FIG. 38. This embodiment rather than being adapted for reception by a tibial trial, has a body 262 with a head 264 adapted for being seated on the base of the recess 212 resected into the tibia and which is dimensioned such that movement of the router when in position in the recess in a generally medial to lateral direction or vice versa is limited. The cutter disk is the same as that utilised on the router shown in FIG. 30 and is arranged for resection of the femur to the desired depth in that bone in the manner described above upon movement of the tibia through an arc of motion about the femur.

In a bicondylar knee arthroplasty method, two small stab incisions are made in the knee with a scalpel blade to provide portals for insertion of a spacer in each one, respectively. The incisions are located medial and lateral to the patellar tendon to allow access to between the tibia and the femur, and are positioned so as to generally not coincide with ligamentous and other soft tissue structures of the knee.

A spacer is then introduced between the opposing lateral condyles and the opposing medial condyles of the tibia and the femur, respectively. The desired thickness of spacers required to obtain balance in the action of relevant ones of the ligaments and other soft tissue structures of the knee during flexion and extension of the tibia relative to the femur to provide appropriate tension in the knee joint and correction of varus or valgus deformity is determined substantially as described above using different thicknessed spacers.

Specifically, the tibia is moved about the femur between forward and backward positions and the kinematics of the knee evaluated. If necessary, one or both of the spacers may be substituted with one(s) of a different thickness and movement of the knee joint while the spacers are in position checked again. This may be repeated a number of times until the optimum spacing of the femur from the tibia is obtained. Accordingly, the spacers selected for optimum spacing of the femur from the tibia may have the same thickness as each other or a different thickness to each other depending on the degree of spacing required between the respective condyle pairs.

The spacers will usually be linked together by a cross-bar during the rotation of the tibia about the femur. The cross-bar may comprise a stiff metal member secured to each spacer by a clamp or suitable fastener respectively, or other such arrangement for inhibiting independent movement of the spacers.

In this way, the desired balancing and deformity correction of the knee joint may be achieved prior to surgically opening the medial and lateral compartments of the knee joint for resection of the medial and lateral condyles of the femur and the tibia.

Once the spacers for providing the optimum spacing of the femur and the tibia have been selected, unicondylar arthroplasty is performed on each of the medial and lateral condyle pairs as described above, one pair at a time. Preferably, the condyle pair deemed to require the greater degree of deformity correction is subjected to arthroplasty first.

More particularly, bone may be resected from the tibia utilising either the tibiofemoral cutting block 38 or guide jig 210 to guide the resection of the bone. Once both the tibial and femoral trials have been fitted, arthroplasty is then performed on the other of the condyle pairs.

Prior to doing so, the spacer selected for spacing of those condyles apart is reinserted between them and the kinematics of the knee joint checked by rotating the tibia about the femur to confirm satisfactory kinematics of the knee joint. Bone is then resected from the tibial and femoral condyles of that pair to the desired depth in each one again utilising the spacer as reference for the positioning of the tibiofemoral cutting block 38 or guide jig 210. Upon fitting of the further tibial and femoral trials, the kinematics of the knee joint are checked once again to ensure adequate range of motion and retention of optimum tension in ligaments and other soft tissue structures of the knee joint. The respective tibial trials and femoral trials are subsequently removed and replaced with the final tibial and femoral prostheses. Generally, the tibial and femoral prostheses will be fitted to one condyle pair at a time.

Accordingly, the bicondylar knee arthroplasty method described comprises performing unicondylar knee arthroplasty as described herein on both medial and lateral condyle pairs of the knee. As will be further appreciated, the bicondylar arthroplasty method involves gently retracting the patella transversely about the knee joint to gain access to the medial or lateral compartment of the knee joint and, subsequently retracting the patella transversely about the knee joint in the opposite direction to gain access to the other of the knee compartments. The method may also allow the quadricep system to remain substantially intact.

Moreover, as with the unicondylar arthroplasty technique described, the bicondylar knee arthroplasty method may allow the desired tensioning and deformity correction to be achieved substantially without the need to transect, elevate or release soft tissue structures of the knee joint although again, adjustment prior to or following fitting of the tibial and femoral trials is not excluded.

Accordingly, although the present invention has been described hereinbefore with reference to preferred embodiments, the skilled addressee will understand that numerous variations and modifications are possible without departing from the scope of the invention.

We claim:

1. An apparatus for removing bone from the femur of a knee joint, comprising:
    a structure mountable within the knee joint; and
    a cutting device seated on the structure and configured to remove bone from the femur in a path of travel of the tibia during operation of the cutting device as the tibia is moved through at least a partial range of motion about the femur between flexed and extended positions.

2. The apparatus of claim 1, wherein the cutting device comprises an upperside, an opposite underside, and a guide member depending from the underside for insertion into a channel of the structure for thereby guiding insertion of the cutting device into the knee joint.

3. The apparatus of claim 1 wherein the structure is a tibial trial or a tibial implant.

4. The apparatus of claim 3, wherein the cutting device is adapted for being mated with the tibial trial or tibial implant for maintaining the proper position of the cutting device relative to the tibial trial or tibial implant during the movement of the tibia about the femur.

5. The apparatus of claim 2, wherein the guide member is profiled for maintaining the proper position of the cutting device relative to the structure as the femur is moved through the range of motion about the tibia.

6. The apparatus of claim 2 wherein the guide member is a depending boss or longitudinally extending key.

7. The apparatus of claim 1 wherein the cutting device comprises a rotatably mounted cutter.

8. The apparatus of claim 7 wherein the cutter is a cutter disk for resecting the bone from the femur.

9. The apparatus of claim 7 wherein the cutter has a concaved upper surface.

10. The apparatus of claim 8 wherein the cutter has a plurality of radially projecting blades for removing the bone from the femur.

11. The apparatus of claim 10 wherein each blade has a cutting edge defined on a leading side of the blade and a further cutting edge on an outer peripheral end of the blade.

12. The apparatus of claim 11 wherein each said blade has a thickness that decreases from the leading side of the blade to a trailing side of the blade.

13. The apparatus of claim 7 wherein the cutter is configured to cut a channel into the femur along the path of travel simultaneously with the removal of the bone.

14. The apparatus of claim 7 wherein the cutter incorporates an upstanding centrally located blade for cutting a channel into the femur along the path of travel simultaneously with the removal of the bone.

15. The apparatus of claim 7 wherein the cutter incorporates a toothed gear for being rotatably driven by a drive mechanism arranged within the cutting device.

16. The apparatus of claim 15 wherein the drive mechanism comprises an end drive that meshes with the toothed gear for driving rotation of the cutter.

17. The apparatus of claim 16 wherein the end drive comprises a screw drive.

18. The apparatus of claim 7, wherein the cutting device further comprises:
    a head carrying the cutter and coupled to a body; and
    the body attachable to a power tool for driving rotation of the cutter.

19. The apparatus of claim 15, wherein the cutting device further comprises:
    a head carrying the cutter and detachably coupled to a body; and
    the body attachable to a power tool for driving rotation of the cutter via the drive mechanism.

20. The apparatus of claim 19 wherein the drive mechanism is arranged in the head and the body incorporates a drive shaft for driving the drive mechanism.

21. The apparatus of claim 18 wherein the head is coupled with the body by a bayonet coupling.

22. The apparatus of claim 20 wherein the drive shaft is coupled with the drive mechanism of the head by a bayonet coupling.

23. The apparatus of claim 1 wherein the cutting device is a head of a router.

24. The apparatus of claim 1 wherein the cutting device is a router.

25. The apparatus of claim 3 wherein the cutting device is adapted to move through at least a partial range of motion between flexed and extended positions on the tibial trial or tibial implant to remove the bone from the femur.

26. The apparatus of claim 1 wherein the cutting device is a rasp.

27. An apparatus for removing bone from the femur of a knee joint, comprising:

a cutting device;
a structure attachable to a bone of the knee joint and configured to receive the cutting device; and
a cutter rotatably mounted on the cutting device and configured to remove bone from the femur in a path of travel of the tibia as the tibia is moved through at least a partial range of motion about the femur between flexed and extended positions.

28. The apparatus of claim 27 wherein the cutter is a cutter disk.

29. The apparatus of claim 27 wherein the cutter has a concaved upper surface.

30. The apparatus of claim 27 wherein the cutter has a plurality of radially projecting blades for removing the bone from the femur.

31. The apparatus of claim 30 wherein each blade has a cutting edge defined on a leading side of the blade and a further cutting edge on an outer peripheral end of the blade.

32. The apparatus of claim 31 wherein each blade has a thickness that decreases from the leading side of the blade to a trailing side of the blade.

33. The apparatus of claim 27 wherein the cutter incorporates an upstanding centrally located blade for cutting a channel into the femur along the path of travel to a greater depth than the desired depth, simultaneously with the removal of the bone.

34. The apparatus of claim 33 wherein the cutter incorporates a cutter drive configured to engage with a drive mechanism for rotatably driving the cutter.

35. The apparatus of claim 34 wherein the drive is a toothed gear.

36. The apparatus of claim 27 wherein the structure is a tibial trial or a tibial implant.

37. A cutter for removing bone from the femur of a knee joint, comprising:
   (a) one or more blades that resects bone from the femur to a desired depth along a path of travel of the tibia with movement of the tibia through at least a partial range of motion about the femur between flexed and extended positions; and
   (b) a further blade that simultaneously cuts a channel into the femur to a greater depth along the path of travel.

38. A cutting device for removing bone to a desired depth from a femur, comprising:
   (a) a body insertable into a knee joint between the femur and the tibia such that the cutting device is seated on a structure mounted within the knee joint;
   (b) a drive mechanism carried by the body that drives rotation of a cutter; and
   (c) the cutter rotatably mounted on the body and configured to remove bone from the femur in a path of travel of the tibia with movement of the tibia through at least a partial range of motion about the femur between flexed and extended positions.

39. A cutting device according to claim 38 wherein the structure is a tibial implant or a tibial instrument.

40. A cutting device according to claim 39 wherein the body mates with the tibial implant or instrument to facilitate alignment in the anterior to posterior direction of the knee joint.

41. A cutting device according to claim 39 wherein the body has an upperside from which the cutter protrudes and an opposite underside that is seated on the tibial implant or instrument.

42. A cutting device for removing bone from the tibia to a desired depth to form a recess in a condyle of the tibia for reception of a tibial implant, comprising:
   (a) a body insertable between the tibia and the femur;
   (b) a cutter rotatably mounted on and protruding from the body, the cutter having side and end cutting edges to remove bone from the tibia to form the recess; and
   (c) a drive mechanism in the body that drives the cutter.

43. A cutting device according to claim 42 wherein the cutter protrudes from the body substantially perpendicularly with respect to a longitudinal axis of the body.

44. A cutting device according to claim 42 wherein the body is adapted for being supported by a support mounted in position about the knee joint, when the cutting device is located in the knee joint between the tibia and the femur.

45. A cutting device according to claim 44 wherein the body incorporates a guide pin for being received in a template disposed in the knee joint for guiding shaping of the recess.

46. An apparatus for removing bone from a femur, comprising:
   a cutter device; and
   a generally planar tibial instrument attachable to a resected surface of a condyle of the tibia and configured to locate the cutter device in a desired orientation relative to the femur as the femur is resected to a desired depth with travel of the tibia about the femur through at least a partial range of motion between the flexed and extended positions.

47. The apparatus of claim 46 wherein the tibial instrument mates with the cutter device to ensure proper positioning of the cutter device relative to the tibial instrument during the movement of the tibia about the femur.

48. The apparatus of claim 46 wherein the tibial instrument has an upperside and an opposite underside, and a feature in the upperside for receiving the cutter device and thereby aligning the cutter device.

49. The apparatus of claim 48 wherein the feature is profiled to ensure proper positioning of the cutter device relative to the tibial instrument during the movement of the tibia about the femur.

50. The apparatus of claim 48 wherein a further feature for aligning the cutter device is defined in the underside of the tibial instrument and which is substantially identical to the feature defined in the upperside of the tibial instrument.

51. The apparatus of claim 46 wherein the tibial instrument is substantially planar in form.

52. The apparatus of claim 46 wherein the tibial instrument is a tibial trial.

* * * * *